United States Patent
Liu et al.

(10) Patent No.: US 10,183,954 B2
(45) Date of Patent: Jan. 22, 2019

(54) OXATHIOLANE CARBOXYLIC ACIDS AND DERIVATIVES FOR THE TREATMENT AND PROPHYLAXIS OF VIRUS INFECTION

(71) Applicant: Hoffmann-La Roche Inc., Little Falls, NJ (US)

(72) Inventors: Haixia Liu, Shanghai (CN); Guolong Wu, Shanghai (CN); Hongying Yun, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/806,635

(22) Filed: Nov. 8, 2017

(65) Prior Publication Data

US 2018/0065991 A1    Mar. 8, 2018

Related U.S. Application Data

(63) Continuation of application No. PCT/EP2016/059949, filed on May 4, 2016.

(51) Int. Cl.
*C07D 513/04* (2006.01)

(52) U.S. Cl.
CPC .................. *C07D 513/04* (2013.01)

(58) Field of Classification Search
CPC .................................................. C07D 513/04
See application file for complete search history.

(56) References Cited

U.S. PATENT DOCUMENTS

| | | |
|---|---|---|
| 5,476,659 A | 12/1995 | Goodman et al. |
| 7,709,448 B2 | 5/2010 | Haley et al. |
| 2005/0004144 A1 | 6/2005 | Carson et al. |

FOREIGN PATENT DOCUMENTS

| | | |
|---|---|---|
| EP | 0343945 | 11/1989 |
| EP | 1072607 | 1/2001 |
| WO | 89/05649 | 6/1989 |
| WO | 98/16184 | 4/1998 |
| WO | 03/020222 A2 | 3/2003 |
| WO | 2005/016235 A2 | 2/2005 |
| WO | 2005/025583 | 3/2005 |
| WO | 2006/066080 A1 | 6/2006 |
| WO | 2007/135134 | 11/2007 |
| WO | 2008/011406 | 1/2008 |
| WO | 2008/140549 | 11/2008 |
| WO | 2009/026292 A1 | 2/2009 |
| WO | 20116/055553 A1 | 4/2016 |

OTHER PUBLICATIONS

Roethle et al., "Identification and Optimization of Pteridinone Toll-like Receptor 7 (TLR7) Agonists for the Oral Treatment of Viral Hepatitis" Journal of Medicinal Chemistry 56(18):7324-7333 (Sep 26, 2013).

*Primary Examiner* — Bruck Kifle
(74) *Attorney, Agent, or Firm* — Jonathan Duffield

(57) ABSTRACT

The present invention relates to compounds of formula (I),

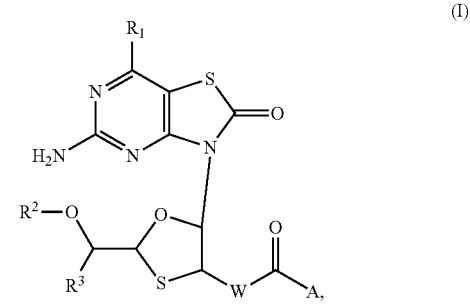

wherein $R^1$, $R^2$ and $R^3$ are as described herein, and their prodrugs or pharmaceutically acceptable salt, enantiomer or diastereomer thereof, and compositions including the compounds and methods of using the compounds.

30 Claims, No Drawings

OXATHIOLANE CARBOXYLIC ACIDS AND DERIVATIVES FOR THE TREATMENT AND PROPHYLAXIS OF VIRUS INFECTION

RELATED APPLICATIONS

This application is a continuation of International Application No. PCT/EP2016/059949, filed May 4, 2016, claiming priority application number PCT/CN2015/078578 filed May 8, 2015, each of which are incorporated herein by reference in its entirety.

The present invention relates to novel oxathiolane carboxylic acids and their corresponding derivatives that have Toll-like receptor agonism activity and their prodrugs thereof, as well as their manufacture, pharmaceutical compositions containing them and their potential use as medicaments.

FIELD OF THE INVENTION

The present invention relates to compounds of formula (I) and (Ia),

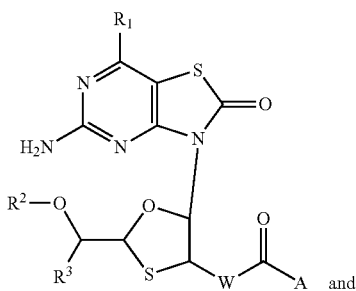

(I)

and

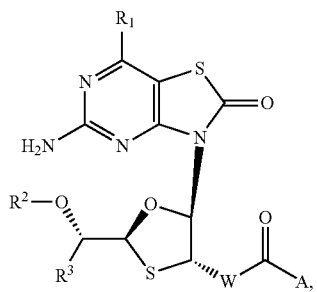

(Ia)

and their prodrugs, compounds of formula (II) and (IIa),

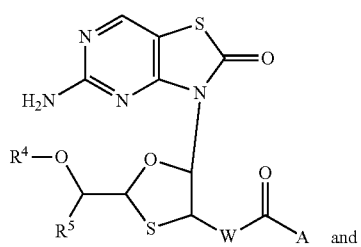

(II)

and

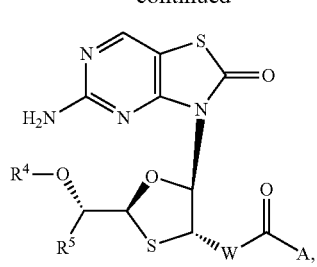

(IIa)

wherein $R^1$ to $R^5$, W and A are described below, or pharmaceutically acceptable salt, enantiomer or diastereomer thereof.

Toll-like receptors (TLRs) detect a wide range of conserved pathogen-associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7 TLR8, and TLR9 are located within endosomes. TLR7 can be activated by binding to a specific small molecule ligand (i.e., TLR7 agonist) or its native ligand (i.e., single-stranded RNA, ssRNA). Following binding of ssRNA to TLR7, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-α and other antiviral cytokine genes. TLR7 is predominately expressed on plasmacytoid cells, and also on B-cells. Altered responsiveness of immune cells might contribute to the reduced innate immune responses during chronic viral infections. Agonist-induced activation of TLR7 might therefore represent a novel approach for the treatment of chronic viral infections. (D. J Connolly and L. A J O'Neill, Current Opinion in Pharmacology 2012, 12:510-518, P. A. Roethle et al, J. Med. Chem. 2013, 56, 7324-7333).

The current therapy of chronic HBV infection is based on two different types of drugs: the traditional antiviral nucleos(t)ide analogues and the more recent Pegylated IFN-α (PEG-IFN-α). The oral nucleos(t)ide analogues act by suppressing the HBV replication. This is a life-long course of treatment during which drug resistance often occurs. As an alternative option, Pegylated IFN-α (PEG-IFN-α) has been used to treat some chronic infected HBV patients within finite therapy duration. Although it has achieved seroconversion in HBeAg at least in a small percentage of HBV patients, the adverse effect makes it poorly tolerable. Notably, functional cure defined as HBsAg seroconversion is very rare with both current therapies. A new generation therapeutic option to treat HBV patients for a functional cure is therefore of urgent need. Treatment with an oral TLR7 agonist represents a promising solution to provide greater efficacy with better tolerability. Pegylated IFN-α (PEG-IFN-α) is currently used to treat chronic HBV and is an alternative to potentially life-long treatment with antiviral nucleos(t)ide analogues. In a subset of chronic HBV patients, PEG-IFN-α therapy can induce sustained immunologic control of the virus following a finite duration of therapy. However, the percentage of HBV patients that achieve seroconversion with interferon therapy is low (up to 27% for HBeAg-positive patients) and the treatment is typically poorly tolerated. Furthermore, functional cure (defined as HBsAg loss and seroconversion) is also very infrequent with both PEG-IFN-α and nucleos(t)ide treatment. Given these limitations, there is an urgent need for improved therapeutic options to treat and induce a functional cure for chronic HBV. Treatment with an oral, small-molecule TLR7 agonist is a promising approach that has the potential to provide greater efficacy and tolerability (T. Asselah et al, Clin Liver Dis 2007, 11, 839-849).

In fact, several identified TLR7 agonists have been considered for therapeutic purposes. So far Imiquimod (ALDARA™) is a U.S. FDA approved TLR7 agonist drug for topical use to treat skin lesions by human papillomavirus. The TLR7/8 dual agonist resiquimod (R-848) and the TLR7 agonist 852A have been evaluated for treating human genital herpes and chemotherapy-refractory metastatic melanoma, respectively. ANA773 is an oral pro-drug TLR7 agonist, developed for the treatment of patients with chronic hepatitis C virus (HCV) infection and chronic hepatitis B infection. GS-9620 is an orally available TLR7 agonist. A phase Ib study demonstrated that treatment with GS-9620 was safe, well tolerated and resulted in dose-dependent ISG15 mRNA induction in patients with chronic hepatitis B (E. J. Gane et al, Annu Meet Am Assoc Study Liver Dis (November 1-5, Washington, D.C.) 2013, Abst 946). Therefore there is high unmet clinical need for developing potent and safe TLR7 agonists as new HBV treatment to offer more therapeutic solutions or replace existing partly effective treatment.

SUMMARY OF THE INVENTION

The present invention provides a series of novel 3-substituted 5-amino-6H-thiazolo[4,5-d]pyrimidine-2,7-dione compounds, that have Toll-like receptor agonism activity and their prodrugs. The invention also provides the bioactivity of such compounds to induce SEAP level increase by activating Toll-like receptors, such as TLR7 receptor, the metabolic conversion of prodrugs to parent compounds in the presence of human hepatocytes, and the therapeutic or prophylactic use of such compounds and their pharmaceutical compositions comprising these compounds and their prodrugs to treat or prevent infectious disease like HBV or HCV. The present invention also provides compounds with superior activity.

The present invention relates to novel compounds of formula (I) and (Ia),

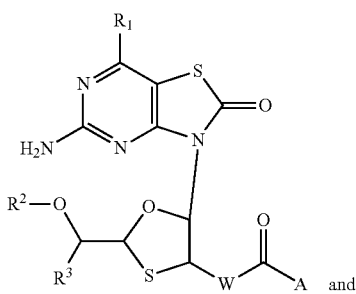

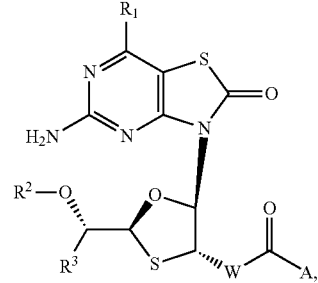

wherein $R^1$ is OH;

$R^2$ is H;

$R^3$ is H, $C_{1-6}$alkyl, $C_{2-6}$alkenyl or $C_{3-7}$cycloalkyl;

W is —$CH_2$— or —$C(C_{1-6}alkyl)_2$-;

A is OH, $C_{1-6}$alkoxy, $C_{1-6}$alkylNH—, $(C_{1-6}alkyl)_2$N— or heterocyclylamino;

or pharmaceutically acceptable salt, enantiomer or diastereomer thereof.

The present invention also relates to the prodrugs of formula (II) and (IIa),

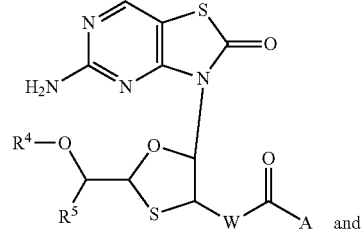

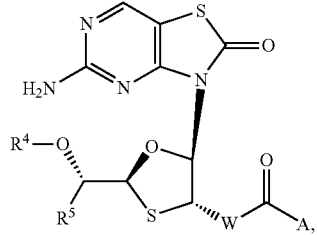

wherein $R^4$ is H, $C_{1-6}$alkylcarbonyl, phenylcarbonyl or $C_{1-6}$alkylphenylcarbonyl;

$R^5$ is H, $C_{1-6}$alkyl, $C_{2-6}$alkenyl or $C_{3-7}$cycloalkyl;

W is —$CH_2$— or —$C(C_{1-6}alkyl)_2$-;

A is OH, $C_{1-6}$alkoxy, $C_{1-6}$alkylNH—, $(C_{1-6}alkyl)_2$N— or heterocyclylamino.

or pharmaceutically acceptable salt, enantiomer or diastereomer thereof.

The invention also relates to their manufacture, medicaments based on a compound in accordance with the invention and their production as well as the use of compounds of formula (I) or (Ia) or their prodrugs, formula (II) or (IIa), thereof as TLR7 agonist. Accordingly, the compounds of formula (I) and (Ia) or their prodrugs of formula (II) and (IIa) are useful for the treatment or prophylaxis of HBV and/or HCV infection with Toll-like receptors agonism.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

As used herein, the term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, iso-butyl, tert-butyl and the like. Particular "$C_{1-6}$alkyl" groups are methyl, ethyl and n-propyl.

The term "heterocyclyl" denotes a monovalent saturated or partly unsaturated mono or bicyclic ring system of 3 to 10 ring atoms, comprising 1 to 5 ring heteroatoms selected from N, O and S, the remaining ring atoms being carbon. In particular embodiments, heterocyclyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydrothienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, dioxothiomorpholinyl, azepanyl, diazepanyl, homopiperazinyl or oxazepanyl. Examples for bicyclic saturated heterocyclyl are azabicyclo[3.2.1]octyl, quinuclidinyl, oxaazabicyclo[3.2.1]octyl, azabicyclo[3.3.1]nonyl, oxaazabicyclo[3.3.1]nonyl, or thiaazabicyclo[3.3.1]nonyl. Examples for partly unsaturated heterocyclyl are dihydrofuryl, imidazolinyl, dihydrooxazolyl, tetrahydropyridinyl or dihydropyranyl.

The term "heterocyclylamino" denotes an amino group with the nitrogen atom on the heterocyclyl ring. Examples of heterocyclylamino are pyrrolidinyl, piperidinyl or morpholinyl.

The term "$C_{2-6}$alkenyl" denotes an unsaturated, linear or branched chain alkenyl group containing 2 to 6, particularly 2 to 4 carbon atoms, for example vinyl, propenyl, allyl, butenyl and the like. Particular "$C_{2-6}$alkenyl" group is allyl and vinyl.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl.

The term "$C_{1-6}$alkoxy" refers to a group $C_{1-6}$alkyl-O—, wherein the "$C_{1-6}$alkyl" is as defined above. Particular "$C_{1-6}$alkoxy" group is methoxy or ethoxy.

The term "carbonyl" alone or in combination refers to the group —C(O)—.

The term "$C_{1-6}$alkylcarbonyl" refers to a group $C_{1-6}$alkyl-C(O)—, wherein the "$C_{1-6}$alkyl" is as defined above. Particular "$C_{1-6}$alkylcarbonyl" group is acetyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Compounds of the general formula (I) or (Ia) and their prodrugs which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

The compounds of the invention may exhibit the phenomenon of tautomerism. While the formula drawings cannot expressly depict all possible tautomeric forms, it is to be understood they are intended to represent any tautomeric form of the depicted compound and are not to be limited merely to a specific compound form depicted by the formula drawings. For example, it is understood for formula (III) that regardless of whether or not the substituents are shown in their enol or their keto form, they represent the same compound (as shown in the example below).

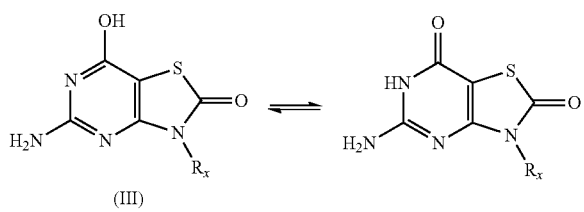

(III)

$R_x$ refers to any feasible substituent.

Some of the compounds of the present invention may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form. As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.). Additionally, compounds of formula (I) and (Ia) and their prodrugs, formula (II) and (IIa), and other compounds of the invention are intended to cover solvated as well as unsolvated forms of the identified structures. For example, formula (I) or (Ia) includes compounds of the indicated structure in both hydrated and non-hydrated forms. Other examples of solvates include the structures in combination with isopropanol, ethanol, methanol, DMSO, ethyl acetate, acetic acid, or ethanolamine.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

TLR7 Agonist and Prodrug

The present invention relates to a compound of formula (I),

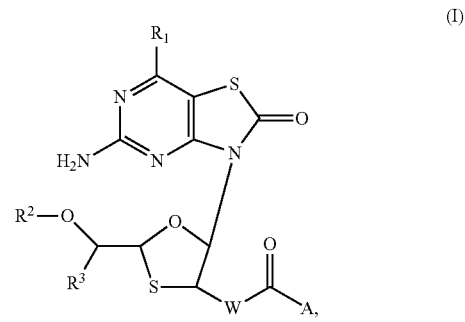

wherein
$R^1$ is OH;
$R^2$ is H;
$R^3$ is H, $C_{1-6}$alkyl, $C_{2-6}$alkenyl or $C_{3-7}$cycloalkyl;
W is —$CH_2$— or —$C(C_{1-6}alkyl)_2$—;
A is OH, $C_{1-6}$alkoxy, $C_{1-6}$alkylNH—, $(C_{1-6}alkyl)_2N$— or heterocyclylamino;
or pharmaceutically acceptable salt, enantiomer or diastereomer thereof.

A further embodiment of present invention is (ii) a compound of formula (I), wherein
$R^1$ is OH;
$R^2$ is H;
$R^3$ is H, methyl, ethyl, butyl, allyl or cyclopropyl;
W is —$CH_2$— or —$C(CH_3)_2$—;
A is OH, methoxy, $CH_3NH$—, $(CH_3)_2N$— or morpholinyl;
or pharmaceutically acceptable salt, enantiomer or diastereomer thereof.

A further embodiment of present invention is (iii) a compound of formula (Ia),

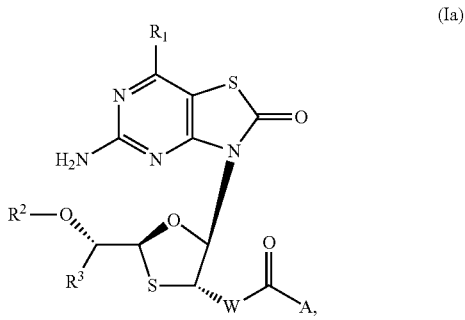

wherein
R¹ is OH;
R² is H;
R³ is H, $C_{1-6}$alkyl, $C_{2-6}$alkenyl or $C_{3-7}$cycloalkyl;
W is —CH₂— or —C($C_{1-6}$alkyl)₂—;
A is OH, $C_{1-6}$alkoxy, $C_{1-6}$alkylNH—, ($C_{1-6}$alkyl)₂N— or heterocyclylamino;
or pharmaceutically acceptable salt, enantiomer or diastereomer thereof.

A further embodiment of present invention is (iv) a compound of formula (Ia), wherein
R¹ is OH;
R² is H;
R³ is H, methyl, ethyl, butyl, allyl or cyclopropyl;
W is —CH₂— or —C(CH₃)₂—;
A is OH, methoxy, CH₃NH—, (CH₃)₂N— or morpholinyl;
or pharmaceutically acceptable salt, enantiomer or diastereomer thereof.

A further embodiment of present invention is (v) a compound of formula (I) or (Ia), wherein R³ is $C_{1-6}$alkyl, $C_{2-6}$alkenyl or $C_{3-7}$cycloalkyl; or pharmaceutically acceptable salt, enantiomer or diastereomer thereof.

A further embodiment of present invention is (vi) a compound of formula (I) or (Ia), wherein R³ is methyl, ethyl, cyclopropyl or allyl; or pharmaceutically acceptable salt, enantiomer or diastereomer thereof.

A further embodiment of present invention is (vii) a compound of formula (I) or (Ia), wherein W is —CH₂—; or pharmaceutically acceptable salt, enantiomer or diastereomer thereof.

A further embodiment of present invention is (viii) a compound of formula (I) or (Ia),
wherein
R¹ is OH;
R² is H;
R³ is $C_{1-6}$alkyl or $C_{3-7}$cycloalkyl;
W is —CH₂—;
A is OH, $C_{1-6}$alkoxy, $C_{1-6}$alkylNH—, ($C_{1-6}$alkyl)₂N— or morpholinyl;
or pharmaceutically acceptable salt, enantiomer or diastereomer thereof.

A further embodiment of present invention is (ix) a compound of formula (I) or (Ia),
wherein
R¹ is OH;
R² is H;
R³ is methyl, ethyl or cyclopropyl;
W is —CH₂—;
A is OH, methoxy, CH₃NH—, (CH₃)₂N— or morpholinyl;
or pharmaceutically acceptable salt, enantiomer or diastereomer thereof.

Another embodiment of present invention is that (x) particular compounds of formula (I) or (Ia) are the following:
Methyl 2-[5-(5-amino-2,7-dioxo-6H-thiazolo[4,5-d]pyrimidin-3-yl)-2-(hydroxymethyl)-1,3-oxathiolan-4-yl]acetate;
Methyl 2-[(trans-2,4-trans-4,5)-5-(5-amino-2,7-dioxo-6H-thiazolo[4,5-d]pyrimidin-3-yl)-2-hydroxymethyl)-1,3-oxathiolan-4-yl]acetate;
2-[5-(5-Amino-2,7-dioxo-6H-thiazolo[4,5-d]pyrimidin-3-yl)-2-(hydroxymethyl)-1,3-oxathiolan-4-yl]acetic acid;
2-[(trans-2,4-trans-4,5)-5-(5-Amino-2,7-dioxo-6H-thiazolo[4,5-d]pyrimidin-3-yl)-2-(hydroxymethyl)-1,3-oxathiolan-4-yl]acetic acid;
2-[5-(5-Amino-2,7-dioxo-6H-thiazolo[4,5-d]pyrimidin-3-yl)-2-(hydroxymethyl)-1,3-oxathiolan-4-yl]-N,N-dimethyl-acetamide;
2-[(trans-2,4-trans-4,5)-5-(5-Amino-2,7-dioxo-6H-thiazolo[4,5-d]pyrimidiin-3-yl)-2-(hydroxymethyl)-1,3-oxathiolan-4-yl]-N,N-dimethyl-acetamide;
Methyl 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate;
Methyl 2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate;
2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid;
2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide;
2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide;
5-Amino-3-[(4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione;
5-Amino-3-[(2S,4S,5R)-2-[(1 S)-1-hydroxypropyl]-4-(2-morpholino-2-oxo-ethyl)-1,3-oxathiolan-5-yl]-6H-thiazolo[4,5-d]pyrimidine-2,7-dione;
Methyl 2-[5-(5-amino-2,7-dioxo-6H-thiazolo[4,5-d]pyrimidin-3-yl)-2-[(1S)-1-hydroxyethyl]-1,3-oxathiolan-4-yl]acetate;
2-[5-(5-Amino-2,7-dioxo-6H-thiazolo[4,5-d]pyrimidin-3-yl)-2-[(1S)-1-hydroxyethyl]-1,3-oxathiolan-4-yl]acetic acid;
2-[5-(5-Amino-2,7-dioxo-6H-thiazolo[4,5-d]pyrimidin-3-yl)-2-[(1S)-1-hydroxypentyl]-1,3-oxathiolan-4-yl]acetic acid;
2-[5-(5-Amino-2,7-dioxo-6H-thiazolo[4,5-d]pyrimidin-3-yl)-2-[(1S)-1-hydroxybut-3-enyl]-1,3-oxathiolan-4-yl] acetic acid;
Methyl 2-[5-(5-amino-2,7-dioxo-6H-thiazolo[4,5-d]pyrimidin-3-yl)-2-[(S)-cyclopropyl(hydroxy)methyl]-1,3-oxathiolan-4-yl]acetate;
2-[5-(5-Amino-2,7-dioxo-6H-thiazolo[4,5-d]pyrimidin-3-yl)-2-[(S)-cyclopropyl(hydroxy)methyl]-1,3-oxathiolan-4-yl]acetic acid;
2-[5-(5-Amino-7-hydroxy-2-oxo-thiazolo[4,5-d]pyrimidin-3-yl)-2-(hydroxymethyl)-1,3-oxathiolan-4-yl]-2-methyl-propanoic acid;
or pharmaceutically acceptable salt, enantiomer or diastereomer thereof.

Another embodiment of present invention is that (xi) more particular compounds of formula (I) or (Ia) are the following:
2-[5-(5-Amino-2,7-dioxo-6H-thiazolo[4,5-d]pyrimidin-3-yl)-2-(hydroxymethyl)-1,3-oxathiolan-4-yl]acetic acid;
2-[(trans-2,4-trans-4,5)-5-(5-amino-2,7-dioxo-6H-thiazolo[4,5-d]pyrimidin-3-yl)-2-(hydroxymethyl)-1,3-oxathiolan-4-yl]acetic acid;
Methyl 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate;

Methyl 2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate;

2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid;

2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid;

2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide;

2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide;

2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide;

2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide;

5-Amino-3-[(4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione;

5-amino-3-[(2S,4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione;

2-[5-(5-Amino-2,7-dioxo-6H-thiazolo[4,5-d]pyrimidin-3-yl)-2-[(1S)-1-hydroxyethyl]-1,3-oxathiolan-4-yl]acetic acid;

2-[5-(5-Amino-2,7-dioxo-6H-thiazolo[4,5-d]pyrimidin-3-yl)-2-[(S)-cyclopropyl(hydroxy)methyl]-1,3-oxathiolan-4-yl]acetic acid;

or pharmaceutically acceptable salt, enantiomer or diastereomer thereof.

Another embodiment of present invention is (xii) a compound of formula (II),

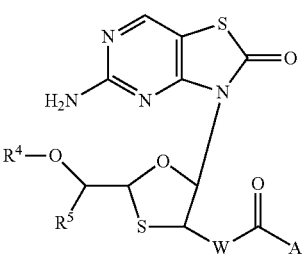

(II)

wherein
$R^4$ is H, $C_{1-6}$alkylcarbonyl, phenylcarbonyl or $C_{1-6}$alkylphenylcarbonyl;
$R^5$ is H, $C_{1-6}$alkyl, $C_{2-6}$alkenyl or $C_{3-7}$cycloalkyl;
W is —$CH_2$— or —$C(C_{1-6}alkyl)_2$-;
A is OH, $C_{1-6}$alkoxy, $C_{1-6}$alkylNH—, $(C_{1-6}alkyl)_2$N— or heterocyclylamino;
or pharmaceutically acceptable salt, enantiomer or diastereomer thereof.

A further embodiment of present invention is (xiii) a compound of formula (II), wherein
$R^4$ is H, acetyl, phenylcarbonyl or methylphenylcarbonyl;
$R^5$ is H, methyl, ethyl, butyl, allyl or cyclopropyl;
W is —$CH_2$— or —$C(CH_3)_2$—;
A is OH, methoxy, $CH_3NH$—, $(CH_3)_2N$— or morpholinyl.
or pharmaceutically acceptable salt, enantiomer or diastereomer thereof.

Another embodiment of present invention is (xiv) a compound of formula (IIa),

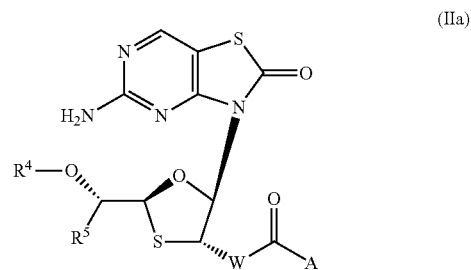

(IIa)

wherein
$R^4$ is H, $C_{1-6}$alkylcarbonyl, phenylcarbonyl or $C_{1-6}$alkylphenylcarbonyl;
$R^5$ is H, $C_{1-6}$alkyl, $C_{2-6}$alkenyl or $C_{3-7}$cycloalkyl;
W is —$CH_2$— or —$C(C_{1-6}alkyl)_2$-;
A is OH, $C_{1-6}$alkoxy, $C_{1-6}$alkylNH—, $(C_{1-6}alkyl)_2$N— or heterocyclylamino;
or pharmaceutically acceptable salt, enantiomer or diastereomer thereof.

A further embodiment of present invention is (xv) a compound of formula (IIa), wherein
$R^4$ is H, acetyl, phenylcarbonyl or methylphenylcarbonyl;
$R^5$ is H, methyl, ethyl, butyl, allyl or cyclopropyl;
W is —$CH_2$— or —$C(CH_3)_2$—;
A is OH, methoxy, $CH_3NH$—, $(CH_3)_2N$— or morpholinyl.
or pharmaceutically acceptable salt, enantiomer or diastereomer thereof.

A further embodiment of present invention is (xvi) a compound of formula (II) or (IIa), wherein $R^4$ is phenylcarbonyl; or pharmaceutically acceptable salt, enantiomer or diastereomer thereof.

A further embodiment of present invention is (xvii) a compound of formula (II) or (IIa), wherein $R^5$ is $C_{1-6}$alkyl, $C_{2-6}$alkenyl or $C_{3-7}$cycloalkyl; or pharmaceutically acceptable salt, enantiomer or diastereomer thereof.

A further embodiment of present invention is (xviii) a compound of formula (II) or (IIa), wherein $R^5$ is methyl, ethyl, cyclopropyl or allyl; or pharmaceutically acceptable salt, enantiomer or diastereomer thereof.

A further embodiment of present invention is (xix) a compound of formula (II) or (IIa), wherein W is —$CH_2$—; or pharmaceutically acceptable salt, enantiomer or diastereomer thereof.

A further embodiment of present invention is (xx) a compound of formula (II) or (IIa),
wherein
$R^4$ is phenylcarbonyl;
$R^5$ is $C_{1-6}$alkyl or $C_{3-7}$cycloalkyl;
W is —$CH_2$—;
A is OH, $C_{1-6}$alkoxy, $C_{1-6}$alkylNH—, $(C_{1-6}alkyl)_2$N— or morpholinyl.
or pharmaceutically acceptable salt, enantiomer or diastereomer thereof.

A further embodiment of present invention is (xxi) a compound of formula (II) or (IIa), wherein
R⁴ is phenylcarbonyl;
R⁵ is methyl, ethyl or cyclopropyl;
W is —CH₂—;
A is OH, methoxy, CH₃NH—, (CH₃)₂N— or morpholinyl.
or pharmaceutically acceptable salt, enantiomer or diastereomer thereof.

Another embodiment of present invention is that (xxii) particular compounds of formula (II) or (IIa) is [(1S)-1-[(2S,4S,5R)-5-(5-amino-2-oxo-thiazolo[4,5-d]pyrimidin-3-yl)-4-(2-methoxy-2-oxo-ethyl)-1,3-oxathiolan-2-yl]propyl]benzoate; or pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, R¹ to R⁵ are as defined above unless otherwise indicated. Furthermore, and unless explicitly otherwise stated, all reactions, reaction conditions, abbreviations and symbols have the meanings well known to a person of ordinary skill in organic chemistry.

Scheme 1:

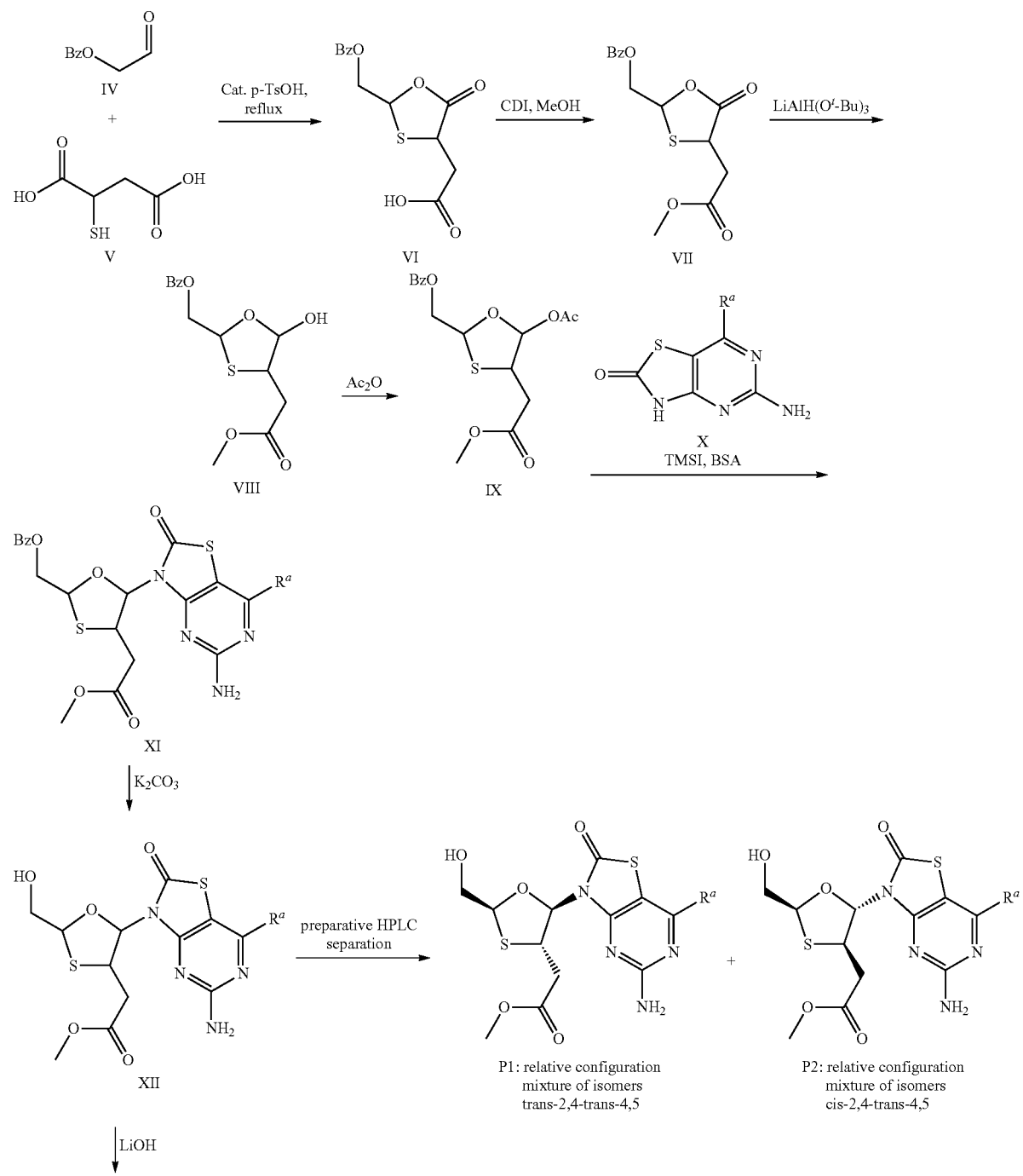

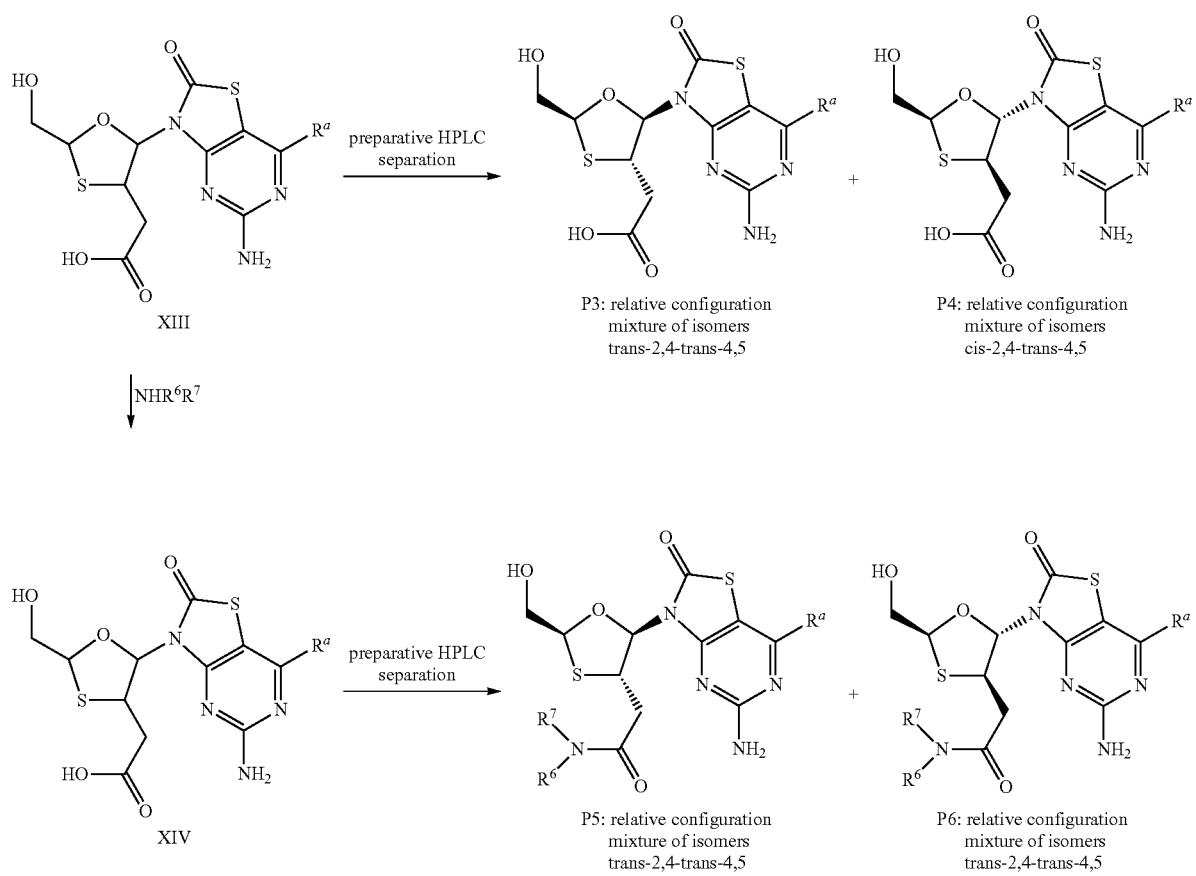

P3: relative configuration mixture of isomers trans-2,4-trans-4,5

P4: relative configuration mixture of isomers cis-2,4-trans-4,5

P5: relative configuration mixture of isomers trans-2,4-trans-4,5

P6: relative configuration mixture of isomers trans-2,4-trans-4,5

$R^a$ is H or $R^1$; $R^6$ and $R^7$ are independently selected from H and $C_{1-6}$ alkyl, or together with nitrogen they are attached to form heterocyclylamino.

As depicted in Scheme 1, the synthesis of the present invention starts from benzoyloxy acetaldehyde IV and mercaptosuccinic acid V, which are refluxed in organic solvent, such as toluene, with catalytic amount of acid, such as p-TsOH, to give carboxylic acid VI. The esterification of the carboxylic acid VI is achieved in the presence of coupling reagent, such as CDI, or with TMSCHN$_2$, to afford ester VII. Ester VII is further reduced with reducing agent, such as LiAlH(Ot-Bu)$_3$, to give hemiacetal VIII. Acylation of the hemiacetal VIII with acid anhydride, such as acetic anhydride, gives compound IX. Coupling of compound IX with compound X in the presence of appropriate silyl etherification agent such as N,O-bis(trimethylsilyl)acetamide (BSA) and Lewis acid such as TMSI gives compound XI. The deprotection of compound XI is achieved under basic condition, such as K$_2$CO$_3$ in MeOH to give compound XII which is further separated by preparative HPLC to give compound P1 and compound P2. Hydrolysis of compound XII under basic condition, such as aqueous LiOH, gives carboxylic acid XIII which is further separated by preparative HPLC to give compound P3 and compound P4. Carboxylic acid XIII is coupled with $R^6R^7NH$ in the presence of coupling reagent, such as HATU, to give amide compound XIV which is further separated by preparative HPLC to give compound P5 and compound P6.

Scheme 2:

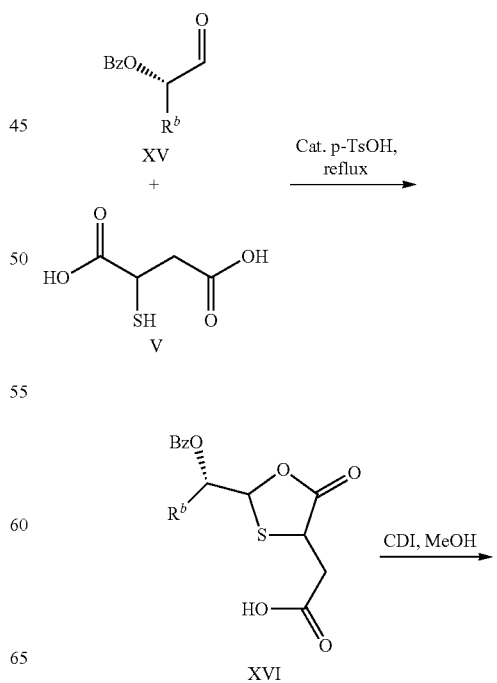

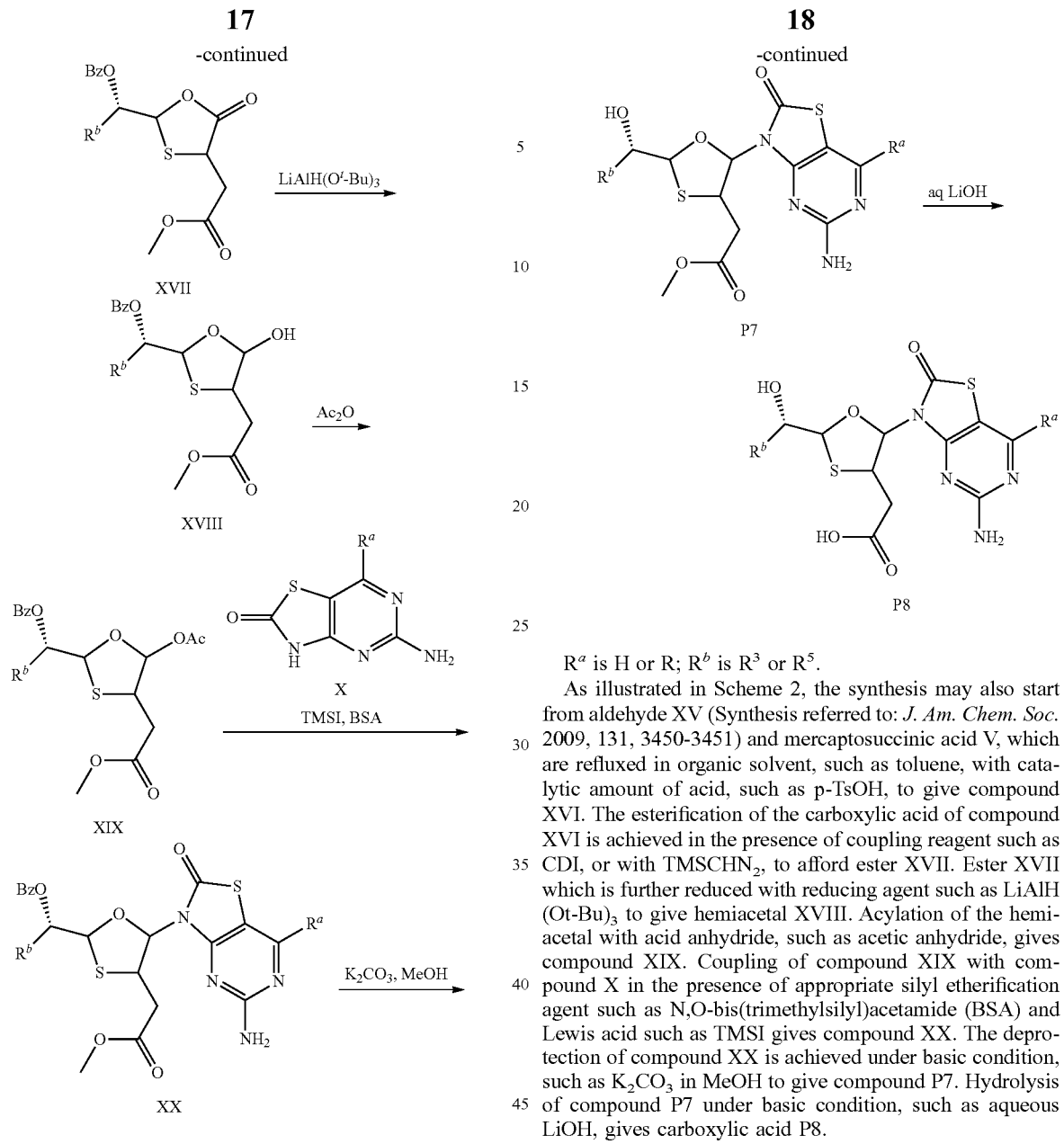

$R^a$ is H or R; $R^b$ is $R^3$ or $R^5$.

As illustrated in Scheme 2, the synthesis may also start from aldehyde XV (Synthesis referred to: *J. Am. Chem. Soc.* 2009, 131, 3450-3451) and mercaptosuccinic acid V, which are refluxed in organic solvent, such as toluene, with catalytic amount of acid, such as p-TsOH, to give compound XVI. The esterification of the carboxylic acid of compound XVI is achieved in the presence of coupling reagent such as CDI, or with $TMSCHN_2$, to afford ester XVII. Ester XVII which is further reduced with reducing agent such as LiAlH(Ot-Bu)$_3$ to give hemiacetal XVIII. Acylation of the hemiacetal with acid anhydride, such as acetic anhydride, gives compound XIX. Coupling of compound XIX with compound X in the presence of appropriate silyl etherification agent such as N,O-bis(trimethylsilyl)acetamide (BSA) and Lewis acid such as TMSI gives compound XX. The deprotection of compound XX is achieved under basic condition, such as $K_2CO_3$ in MeOH to give compound P7. Hydrolysis of compound P7 under basic condition, such as aqueous LiOH, gives carboxylic acid P8.

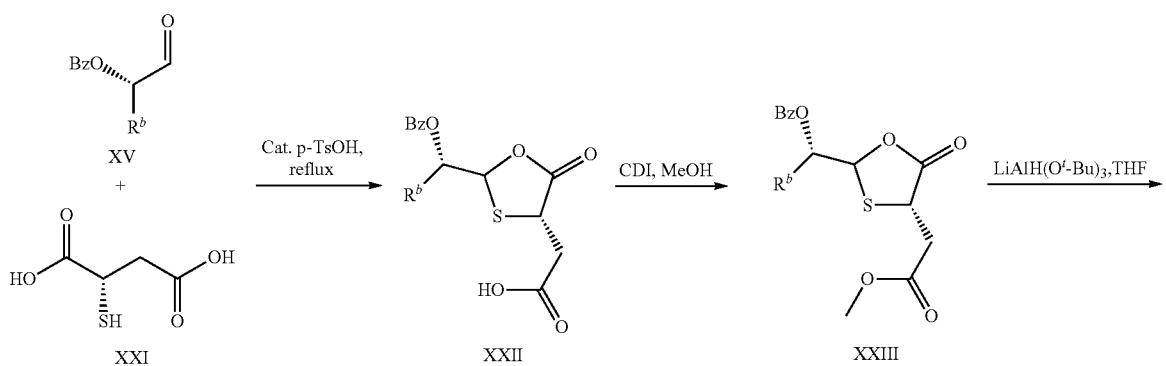

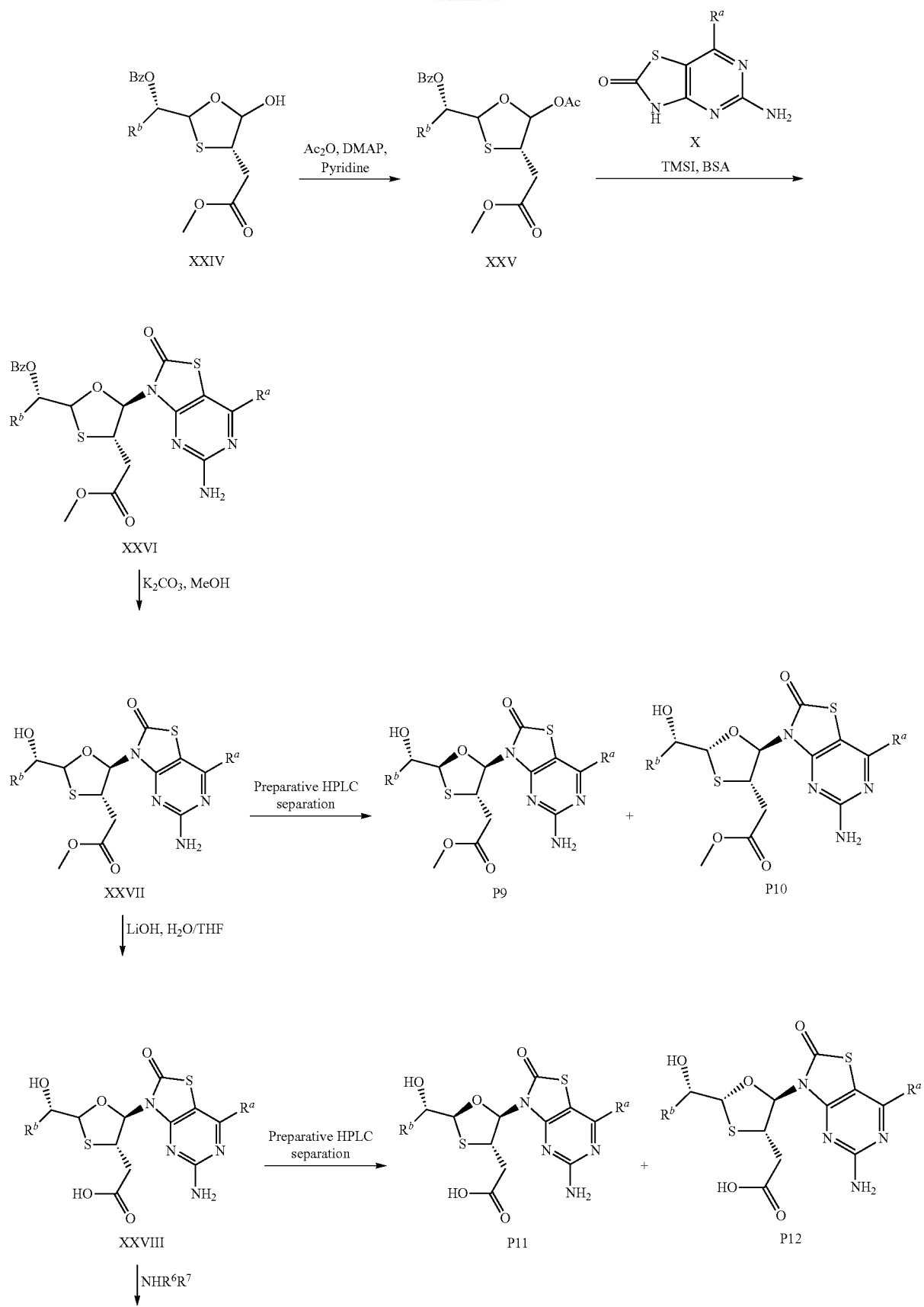

-continued

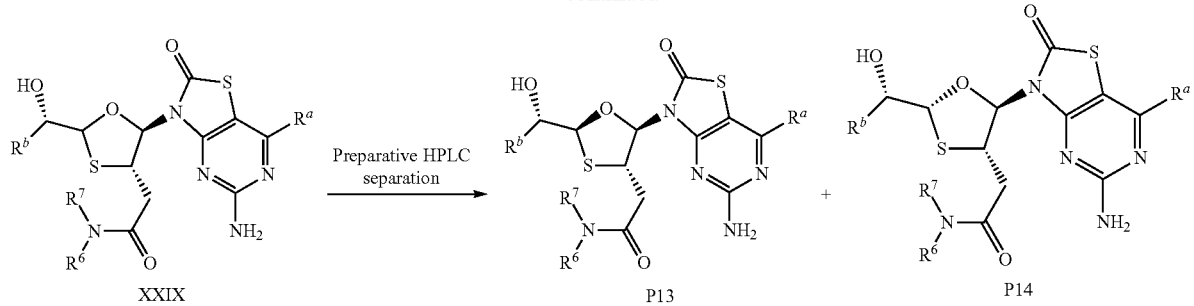

$R^a$ is H or $R^1$; $R^b$ is $R^3$ or $R^5$; $R^6$ and $R^7$ are independently selected from H and $C_{1-6}$alkyl, or together with nitrogen they are attached to form heterocyclylamino.

As illustrated in Scheme 3, alternatively, the synthesis may also start from aldehyde XV (Synthesis referred to: *J. Am. Chem. Soc.* 2009, 131, 3450-3451) and (S)-2-mercaptosuccinic acid XXI, which are refluxed in organic solvent, such as toluene, with catalytic amount of acid, such asp-TsOH, to give compound XXII. The esterification of the carboxylic acid XXII is achieved in the presence of coupling reagent, such as CDI, or with $TMSCHN_2$, to afford ester XXIII. Ester XXIII is further reduced with reducing agent such as $LiAlH(Ot-Bu)_3$ to give hemiacetal XXIV. Acylation of the hemiacetal XXIV with acid anhydride, such as acetic anhydride, gives compound XXV. Coupling of compound XXV with compound X in the presence of appropriate silyl etherification agent such as N,O-bis(trimethylsilyl)acetamide (BSA) and Lewis acid such as TMSI gives compound XXVI. The deprotection of compound XXVI is achieved under basic condition such as $K_2CO_3$ in MeOH to give compound XXVII which is further separated by preparative HPLC to give compound P9 and compound P10. Hydrolysis of compound XXVII under basic condition, such as aqueous LiOH, gives carboxylic acid XXVIII which is further separated by preparative HPLC to give compound P11 and compound P12. Carboxylic acid XXVIII is coupled with $R^6R^7NH$ in the presence of coupling reagent, such as HATU, to give amide compound XXIX which is further separated by preparative HPLC to give compound P13 and compound P14.

This invention also relates to a process for the preparation of a compound of formula (I), (Ia), (II) or (IIa) comprising the reaction of:

(a) the reaction of a compound of formula (XI),

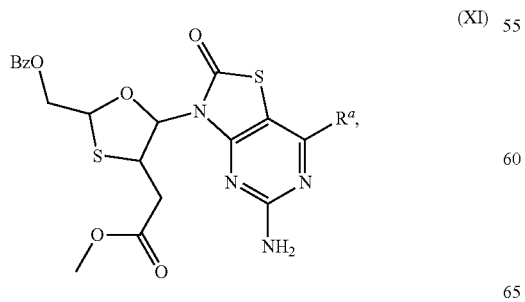

(XI)

with a base, wherein $R^a$ is H or $R^1$;

(b) the reaction of a compound of formula (XII),

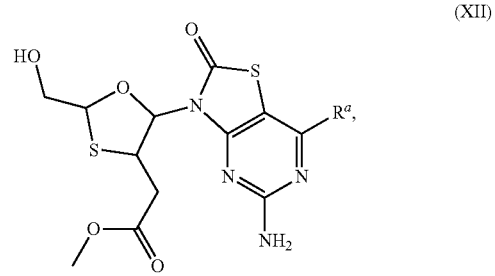

(XII)

with a base, wherein $R^a$ is H or $R^1$;

(c) the reaction of a compound of formula (XIII),

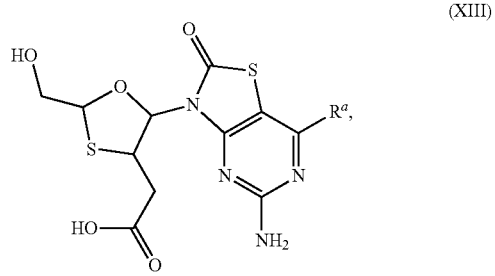

(XIII)

with $R^6R^7NH$ in the presence of coupling reagent, wherein $R^a$ is H or $R^1$;

(d) the reaction of a compound of formula (P7),

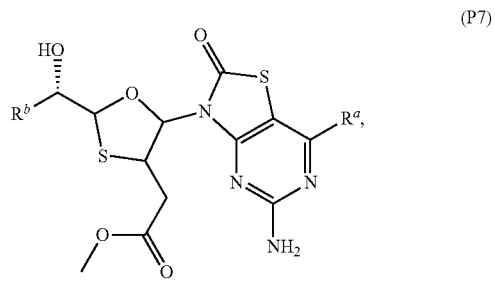

(P7)

with a base, wherein $R^a$ is H or $R^1$; $R^b$ is $R^3$ or $R^5$;

(e) the reaction of a compound of formula (XXVI),

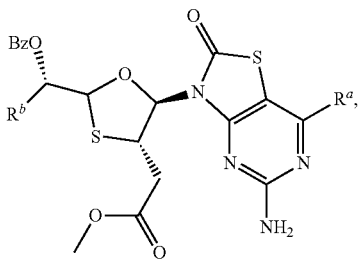
(XXVI)

with a base, wherein $R^a$ is H or $R^1$; $R^b$ is $R^3$ or $R^5$;
(f) the reaction of a compound of formula (XXVII),

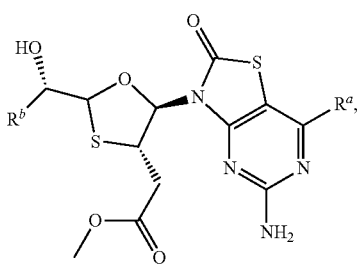
(XXVII)

with a base, wherein $R^a$ is H or $R^1$; $R^b$ is $R^3$ or $R^5$;
(g) the reaction of a compound of formula (XXVIII),

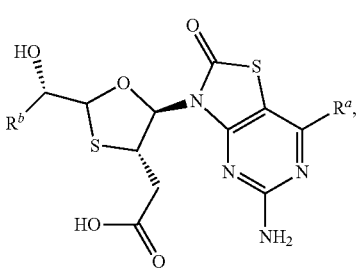
(XXVIII)

with $R^6R^7NH$ in the presence of coupling reagent, wherein $R^a$ is H or $R^1$; $R^b$ is $R^3$ or $R^5$;
(h) the reaction of a compound of formula (XXV),

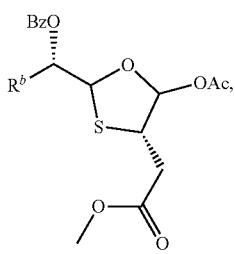
(XXV)

with compound X in the presence of silyl etherification agent and Lewis acid, wherein $R^b$ is $R^3$ or $R^5$;
or wherein $R^a$, $R^b$, $R^1$, $R^2$, $R^3$, $R^5$, $R^6$ and $R^7$ are defined above.

In step (a) and (e), the base can be for example $K_2CO_3$.
In step (b), (d) and (f), the base can be for example LiOH.
In step (c) and (g), the coupling reagent can be for example HATU.
In step (h), the silyl etherification agent can be for example BSA, and Lewis acid can be for example TMSI.

A compound of formula (I), (Ia), (II) and (IIa) when manufactured according to the above process is also an object of the invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) or (Ia) or their prodrugs may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) or (Ia) or their prodrugs are formulated in an acetate buffer, at pH 5. In another embodiment, the compounds of formula (I) or (Ia) or their prodrugs are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to activate TLR7 receptor and lead to produce INF-α and other cytokines, which can be used, but not limited, for the treatment or prevention of hepatitis B and/or C viral infected patients.

In one example, the pharmaceutically effective amount of the compound of the invention administered parenterally per dose will be in the range of about 0.1 to 50 mg/kg, alternatively about 0.1 to 30 mg/kg of patient body weight per day, with the typical initial range of compound used being 0.3 to 15 mg/kg/day. In another embodiment, oral unit dosage forms, such as tablets and capsules, preferably contain from about 20 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 20 to 1000 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 20 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of formula (I) or (Ia) or their prodrugs, formula (II) or (IIa), or pharmaceutically acceptable salts or enantiomers or diastereomers thereof.

In a further embodiment includes a pharmaceutical composition comprising a compound of formula (I) or (Ia) or their prodrugs, formula (II) or (IIa), or pharmaceutically acceptable salts or enantiomers or diastereomers thereof, together with a pharmaceutically acceptable carrier or excipient.

Another embodiment includes a pharmaceutical composition comprising a compound of formula (I) or (Ia) or their prodrugs, formula (II) or (IIa), or pharmaceutically acceptable salts or enantiomers or diastereomers thereof for use in the treatment of hepatitis B virus infection.

Indications and Methods of Treatment

The present invention provides methods for treating or preventing a hepatitis B viral infection and/or hepatitis C viral infection in a patient in need thereof.

The present invention further provides methods for introducing a therapeutically effective amount of a formula (I) or (Ia) compounds or their prodrugs, or other compounds of the invention into the blood stream of a patient in the treatment and/or prevention of hepatitis B and/or C viral infection.

The methods of the present invention are particularly well suited for human patients. In particular, the methods and doses of the present invention can be useful for, but not limited to, HBV and/or HCV infected patients. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Another embodiment includes a method of treating or preventing hepatitis B viral infection and/or hepatitis C viral infection in a mammal in need of such treatment, wherein the method comprises administering to said mammal a therapeutically effective amount of a compound of formula (I) or (Ia) or their prodrugs, or enantiomers, diastereomers, prodrugs or pharmaceutically acceptable salts thereof.

EXAMPLES

The invention will be more fully understood by reference to the following examples. They should not, however, be construed as limiting the scope of the invention.

Abbreviations

ACN: acetonitrile
HATU: 1-[bis(dimethylamino)methylene]-1H-1,2,3-triazolo[4,5-b]pyridinium 3-oxid hexafluorophosphate
DMAP: 4-dimethylaminopyridine
DIPEA: diisopropylethylamine
p-TsOH: 4-methylbenzenesulfonic acid
DMSO-$d_6$: deuterated dimethylsulfoxide
DCM: dichloromethane
FBS: fetal bovine serum
rt: room temperature
HPLC: high performance liquid chromatography
LiAlH(Ot-Bu)$_3$: lithium tri-tert-butoxyaluminum hydride
v/v: volume ratio
SFC: supercritical fluid chromatography
MS (ESI): mass spectroscopy (electron spray ionization)
BSA: N, O-bis(trimethylsilyl)acetamide
obsd.: observed
$EC_{50}$: the molar concentration of an agonist, which produces 50% of the maximum possible response for that agonist.
TEA: triethylamine
TMSCHN$_2$: trimethylsilyl diazomethane
TMSI: trimethylsilyl iodide
CDI: 1,1'-carbonyldiimidazole
TMSCl: trimethylsilyl chloride
NBS: N-bromosuccinimide General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™

Perp C$_{18}$ (5 μm, OBD™ 30×100 mm) column or SunFire™ Perp C$_{18}$ (5 μm, OBD™ 30×100 mm) column.

LC/MS spectra were obtained using a Waters UPLC-SQD Mass. Standard LC/MS conditions were as follows (running time 3 minutes):

Acidic condition: A: 0.1% formic acid and 1% acetonitrile in H$_2$O; B: 0.1% formic acid in acetonitrile;
Basic condition: A: 0.05% NH$_3$.H$_2$O in H$_2$O; B: acetonitrile.

Mass spectra (MS): generally only ions which indicate the parent mass are reported, and unless otherwise stated the mass ion quoted is the positive mass ion (M+H)$^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

PREPARATIVE EXAMPLES

Example 1

Methyl 2-[5-(5-amino-2,7-dioxo-6H-thiazolo[4,5-d]pyrimidin-3-yl)-2-(hydroxymethyl)-1,3-oxathiolan-4-yl]acetate

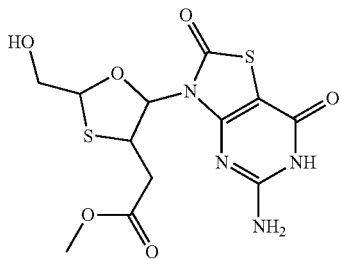 [SMILES: COC(=O)CC1SC(CO)OC1n1c(=O)sc2c(=O)[nH]c(N)nc21]

Preparation of 2-[2-(benzoyloxymethyl)-5-oxo-1,3-oxathiolan-4-yl]acetic acid (Compound 1a)

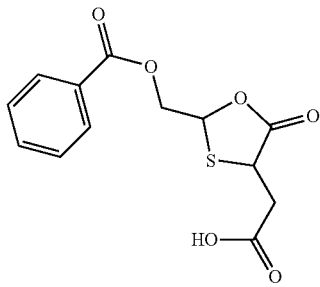 [SMILES: O=C(O)CC1SC(COC(=O)c2ccccc2)OC1=O]

A mixture of benzoyloxy acetaldehyde (1.97 g, 12 mmol) and mercaptosuccinic acid (1.5 g, 10 mmol) was stirred at 60° C. in toluene (50 mL) under catalytic amount of p-TsOH (0.23 g, 1.3 mmol) for 4 h. After the reaction was completed, the mixture was cooled to rt and diluted with EtOAc (50 mL), washed with saturated NaHCO$_3$ and brine. The organic layer was dried over Na$_2$SO$_4$, filtered and concentrated to give the crude product which was purified by column chromatography to give 2-[2-(benzoyloxymethyl)-5-oxo-1,3-oxathiolan-4-yl]acetic acid (compound 1a) 2.5 g as a white powder.

Compound 1a: $^1$H NMR (400 MHz, DMSO-d$_6$) δ ppm: 12.78 (brs, 1H), 7.99 (m, 2H), 7.70 (m, 1H), 7.57 (m, 2H), 5.92 (t, J=4.8 Hz, 1H), 4.53-4.65 (m, 2H), 4.42-4.53 (m, 1H), 2.72-3.06 (m, 2H). MS obsd. (ESI$^+$) [(M+H)$^+$]: 297.

Preparation of [4-(2-methoxy-2-oxo-ethyl)-5-oxo-1,3-oxathiolan-2-yl]methyl benzoate (compound 1b)

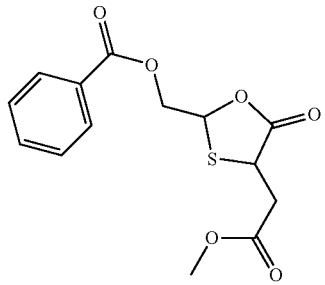 [SMILES: COC(=O)CC1SC(COC(=O)c2ccccc2)OC1=O]

To the solution of 2-[2-(benzoyloxymethyl)-5-oxo-1,3-oxathiolan-4-yl]acetic acid (compound 1a) (1.5 g, 5.1 mmol) in DCM (20 mL) was added CDI (1.23 g, 7.6 mmol). The mixture was stirred at rt for 3 h, then MeOH (0.62 mL, 15 mmol) was added. The mixture was stirred at rt for another 16 h. After the reaction was completed, the reaction mixture was quenched with saturated NH$_4$Cl, extracted with DCM. The combined organic layer was washed with saturated NH$_4$Cl and brine, dried over Na$_2$SO$_4$, filtered and concentrated to give the crude product which was purified by column chromatography to afford [4-(2-methoxy-2-oxo-ethyl)-5-oxo-1,3-oxathiolan-2-yl]methyl benzoate (compound 1b) 0.83 g as a yellowish oil.

Compound 1b: $^1$H NMR (400 MHz, CDCl$_3$) δ ppm: 8.05 (m, 2H), 7.62 (m, 1H), 7.48 (m, 2H), 5.74-5.86 (m, 1H), 4.60 (m, 2H), 4.30-4.40 (m, 1H), 3.77 (m, 3H), 2.97-3.24 (m, 2H). MS obsd. (ESI$^+$) [(M+H)$^+$]: 311.

Preparation of [5-acetoxy-4-(2-methoxy-2-oxo-ethyl)-1,3-oxathiolan-2-yl]methyl benzoate (compound 1c)

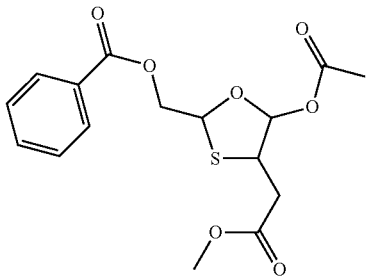 [SMILES: COC(=O)CC1SC(COC(=O)c2ccccc2)OC1OC(C)=O]

To a solution of [4-(2-methoxy-2-oxo-ethyl)-5-oxo-1,3-oxathiolan-2-yl]methyl benzoate (compound 1b) (600 mg, 1.9 mmol) in anhydrous THF (10 mL) was added LiAlH(Ot-Bu)$_3$ (1 M in THF, 2.9 mL, 2.9 mmol) dropwise at −78° C. After being stirred at rt for 2 h, pyridine (0.78 mL, 9.6 mmol), acetic anhydride (0.91 mL, 9.6 mmol) and DMAP (0.71 g, 5.8 mmol) were added. The reaction mixture was stirred at rt overnight and then quenched with saturated NH$_4$Cl. The solution was extracted with DCM (50 mL) three times. The organic layer was combined, washed with brine, dried over Na$_2$SO$_4$, filtered and concentrated to give the crude product which was purified by flash column chromatography to afford [5-acetoxy-4-(2-methoxy-2-oxo-ethyl)-1,3-oxathiolan-2-yl]methyl benzoate (compound 1c) 0.34 g as a yellowish oil.

Compound 1c: $^1$H NMR (400 MHz, CDCl$_3$) δ ppm: 8.08 (m, 2H), 7.59 (m, 1H), 7.47 (m, 2H), 6.42-6.73 (m, 1H), 5.65-5.77 (m, 1H), 4.50-4.70 (m, 1H), 4.34-4.42 (m, 1H), 3.90-4.03 (m, 1H), 3.67-3.78 (m, 3H), 2.58-2.91 (m, 2H), 2.06-2.18 (m, 3H). MS obsd. (ESI$^+$) [(M+H)$^+$]: 355.

Preparation of [5-(5-amino-2,7-dioxo-6H-thiazolo[4,5-d]pyrimidin-3-yl)-4-(2-methoxy-2-oxo-ethyl)-1,3-oxathiolan-2-yl]methyl benzoate (compound 1d)

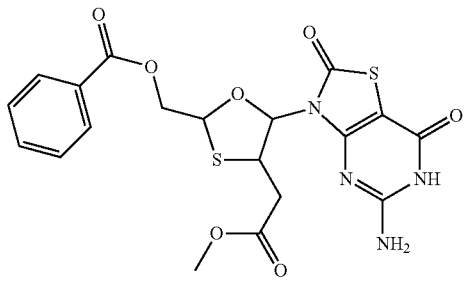 [SMILES: COC(=O)CC1SC(COC(=O)c2ccccc2)OC1n1c(=O)sc2c(=O)[nH]c(N)nc21]

To a solution of 5-amino-7-hydroxy-3H-thiazolo[4,5-d]pyrimidin-2-one (368 mg, 2.0 mmol) in ACN (15 mL) was added BSA (1.42 g, 7.0 mmol). The mixture was heated at 60° C. until a clear solution was formed. The solvent was removed under reduced pressure. The residue was dissolved in DCM (20 mL). To the above solution were added [5-acetoxy-4-(2-methoxy-2-oxo-ethyl)-1,3-oxathiolan-2-yl]methyl benzoate (compound 1c) (700 mg, 2.0 mmol) and TMSI (0.61 mL, 4.4 mmol). After being stirred at rt overnight, the reaction mixture was quenched with saturated NaHCO$_3$ solution. The mixture was extracted with DCM (100 mL) three times. The combined organic layer was washed with saturated NaHCO$_3$ and brine, dried over Na$_2$SO$_4$, filtered and concentrated to give the crude product which was purified by flash column chromatography on silica gel to afford [5-(5-amino-2,7-dioxo-6H-thiazolo[4,5-d]pyrimidin-3-yl)-4-(2-methoxy-2-oxo-ethyl)-1,3-oxathiolan-2-yl]methyl benzoate (compound 1d) 0.22 g as a light yellow powder. MS obsd. (ESI$^+$) [(M+H)$^+$]: 479.

Preparation of methyl 2-[5-(5-amino-2,7-dioxo-6H-thiazolo[4,5-d]pyrimidin-3-yl)-2-(hydroxymethyl)-1,3-oxathiolan-4-yl]acetate (Example 1)

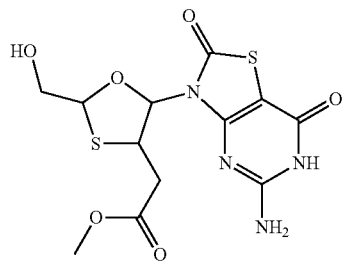 [SMILES: COC(=O)CC1SC(CO)OC1n1c(=O)sc2c(=O)[nH]c(N)nc21]

To the solution of [5-(5-amino-2,7-dioxo-6H-thiazolo[4,5-d]pyrimidin-3-yl)-4-(2-methoxy-2-oxo-ethyl)-1,3-oxathiolan-2-yl]methyl benzoate (compound 1d) (180 mg, 0.38 mmol) in MeOH (10 mL) was added K$_2$CO$_3$ (0.21 g, 1.5 mmol). The mixture was stirred at rt. After the reaction was completed, the mixture was neutralized to pH 7 with HOAc, then concentrated to give the crude product which was purified by preparative HPLC to afford methyl 2-[(trans-2,4-trans-4,5)-5-(5-amino-2,7-dioxo-6H-thiazolo[4,5-d]pyrimidin-3-yl)-2-hydroxymethyl)-1,3-oxathiolan-4-yl]acetate (Example 1-P1) 2 mg and methyl 2-[(cis-2,4-trans-4,5)-5-(5-amino-2,7-dioxo-6H-thiazolo[4,5-d]pyrimidin-3-yl)-2-hydroxymethyl)-1,3-oxathiolan-4-yl]acetate (Example 1-P2) 4 mg as white powders. The relative configuration of Example 1-P1 and Example 1-P2 were determined in analogy to Example 2.

Example 1-P1

$^1$H NMR (400 MHz, CD$_3$OD) δ ppm: 5.96 (d, J=8.5 Hz, 1H), 5.29 (dd, J=5.5, 4.3 Hz, 1H), 4.86 (m, 1H), 3.83 (m, 1H), 3.75 (m, 1H), 3.61 (s, 3H), 2.76 (d, J=7.3 Hz, 2H). MS obsd. (ESI$^+$) [(M+H)$^+$]: 375.

Example 1-P2

$^1$H NMR (400 MHz, CD$_3$OD) δ ppm: 6.14 (d, J=7.0 Hz, 1H), 5.78 (dd, J=5.3, 4.0 Hz, 1H), 4.83 (m, 1H), 3.75 (m, 2H), 3.61 (s, 3H), 2.82 (m, 2H). MS obsd. (ESI$^+$) [(M+H)$^+$]: 375.

Example 2

2-[5-(5-Amino-2,7-dioxo-6H-thiazolo[4,5-d]pyrimidin-3-yl)-2-(hydroxymethyl)-1,3-oxathiolan-4-yl]acetic acid

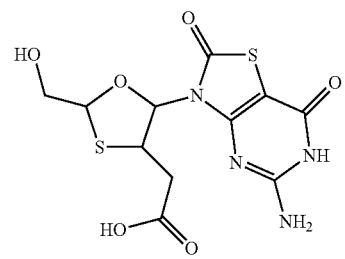 [SMILES: Nc1nc2c(sc(=O)n2C2OC(CO)SC2CC(=O)O)c(=O)[nH]1]

Preparation of 2-[5-(5-amino-2,7-dioxo-6H-thiazolo[4,5-d]pyrimidin-3-yl)-2-(hydroxymethyl)-1,3-oxathiolan-4-yl]acetic acid (Example 2)

To the solution of crude methyl 2-[5-(5-amino-2,7-dioxo-6H-thiazolo[4,5-d]pyrimidin-3-yl)-2-(hydroxymethyl)-1,3-oxathiolan-4-yl]acetate (Example 1) (168 mg, 0.45 mmol) in THF (10 mL) was added aqueous LiOH (2 M, 5 mL, 1.0 mmol). The reaction mixture was stirred at rt. After the reaction was completed, the mixture was neutralized to pH 7 with HOAc, concentrated to give the crude product which was purified by preparative HPLC to afford 2-[(trans-2,4-trans-4,5)-5-(5-amino-2,7-dioxo-6H-thiazolo[4,5-d]pyrimidin-3-yl)-2-(hydroxymethyl)-1,3-oxathiolan-4-yl]acetic acid (Example 2-P1) 8 mg and 2-[(cis-2,4-trans-4,5)-5-(5-amino-2,7-dioxo-6H-thiazolo[4,5-d]pyrimidin-3-yl)-2-(hydroxymethyl)-1,3-oxathiolan-4-yl]acetic acid (Example 2-P2) 17 mg as white powders. The relative configuration of compound Example 2-P1 and Example 2-P2 were determined by NOESY.

Example 2-P1

$^1$H NMR (400 MHz, CD$_3$OD) δ ppm: 5.96 (d, J=8.5 Hz, 1H), 5.28 (dd, J=5.5, 4.0 Hz, 1H), 4.85 (m, 1H), 3.83 (m, 1H), 3.75 (m, 1H), 2.67 (m, 2H). MS obsd. (ESI$^+$) [(M+H)$^+$]: 361.

Example 2-P2

$^1$H NMR (400 MHz, CD$_3$OD) δ ppm: 6.13 (d, J=7.0 Hz, 1H), 5.77 (dd, J=5.5, 4.3 Hz, 1H), 4.83 (m, 1H), 3.75 (m, 2H), 2.77 (m, 1H), 2.66 (m, 1H). MS obsd. (ESI$^+$) [(M+H)$^+$]: 361.

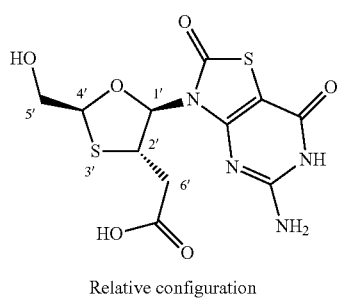

Example 2-P1

Relative configuration

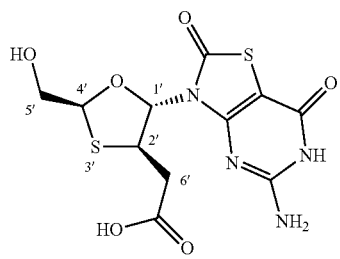

Example 2-P2

Relative configuration

For Example 2-P1, the NOESY correlation of C1'-H and C4'-H, C1'-H and C6'-H were observed, no correlation of C2'-H and C4'-H was observed. For Example 2-P2, the NOESY correlation of C2'-H and C4'-H, C1'-H and C6'-H were observed, no correlation of C1'-H and C4'-H was observed.

Example 3

2-[5-(5-Amino-2,7-dioxo-6H-thiazolo[4,5-d]pyrimidin-3-yl)-2-(hydroxymethyl)-1,3-oxathiolan-4-yl]-N,N-dimethyl-acetamide

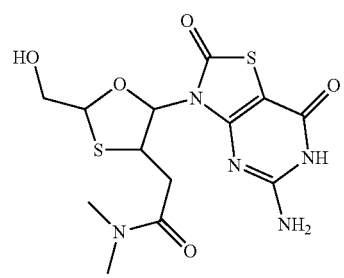 [SMILES: CN(C)C(=O)CC1SC(CO)OC1n1c(=O)sc2c(=O)[nH]c(N)nc21]

Preparation of 2-[5-(5-amino-2,7-dioxo-6H-thiazolo[4,5-d]pyrimidin-3-yl)-2-(hydroxymethyl)-1,3-oxathiolan-4-yl]-N,N-dimethyl-acetamide To the solution of crude 2-[5-(5-amino-2,7-dioxo-6H-thiazolo[4,5-d]pyrimidin-3-yl)-2-(hydroxymethyl)-1,3-oxathiolan-4-yl]acetic acid (Example 2) (133 mg, 0.37 mol), dimethylamine (0.22 mL, 0.45 mol) and DIPEA (0.3 mL, 1.5 mmol) in DMF (5 mL) was added HATU (214 mg, 0.56 mmol). The reaction mixture was stirred at rt for 1 h, quenched with saturated NH$_4$Cl, extracted with EtOAc. The combined organic layer was washed with brine, dried over Na$_2$SO$_4$, filtered and concentrated to give the crude product which was purified by preparative HPLC to give 2-[(trans-2,4-trans-4,5)-5-(5-amino-2,7-dioxo-6H-thiazolo[4,5-d]pyrimidin-3-yl)-2-(hydroxymethyl)-1,3-oxathiolan-4-yl]-N,N-dimethyl-acetamide (Example 3-P1) 6 mg and 2-[(cis-2,4-trans-4,5)-5-(5-amino-2,7-dioxo-6H-thiazolo[4,5-d]pyrimidin-3-yl)-2-(hydroxymethyl)-1,3-oxathiolan-4-yl]-N,N-dimethyl-acetamide (Example 3-P2) 10 mg as white powders. The relative configuration of compound Example 3-P1 and Example 3-P2 were determined in analogy to Example 2.

Example 3-P1

$^1$H NMR (400 MHz, CD$_3$OD) δ ppm: 5.96 (d, J=8.8 Hz, 1H), 5.28 (dd, J=5.3, 4.02 Hz, 1H), 4.95 (m, 1H), 3.79 (m, 2H), 3.03 (s, 3H), 2.88 (m, 1H), 2.84 (s, 3H), 2.76 (m, 1H). MS obsd. (ESI$^+$) [(M+H)$^+$]: 388.

Example 3-P2

$^1$H NMR (400 MHz, CD$_3$OD) δ ppm: 6.13 (d, J=7.0 Hz, 1H), 5.76 (t, J=4.6 Hz, 1H), 4.86 (m, 1H), 3.75 (m, 2H), 3.05 (s, 3H), 2.95 (m, 1H), 2.86 (s, 3H), 2.83 (m, 1H). MS obsd. (ESI$^+$) [(M+H)$^+$]: 388.

Example 4

Methyl 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate

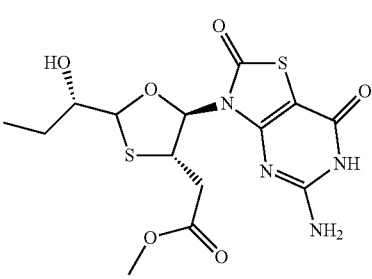 [SMILES: CC[C@H](O)C1O[C@@H](n2c(=O)sc3c(=O)[nH]c(N)nc32)[C@H](CC(=O)OC)S1]

Preparation of 2-[(4S)-2-[(1S)-1-benzoyloxypropyl]-5-oxo-1,3-oxathiolan-4-yl]acetic acid (compound 4a)

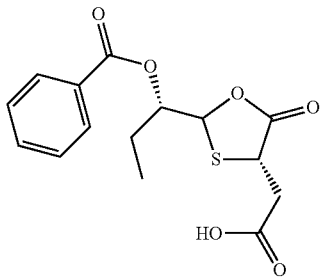 [SMILES: CC[C@H](OC(=O)c1ccccc1)C1OC(=O)[C@H](CC(=O)O)S1]

A mixture of [(1S)-1-formylpropyl]benzoate (4.6 g, 24 mmol) (Synthesis referred to: *J. Am. Chem. Soc.* 2009, 131, 3450-3451.), (S)-2-mercaptosuccinic acid (3.59 g, 24 mmol) and p-TsOH (455 mg, 2.4 mmol) in toluene (200 mL) was stirred at 60° C. for 4 h. After the reaction was completed, the mixture was diluted with EtOAc (100 mL), washed with saturated NaHCO$_3$ and brine, dried over Na$_2$SO$_4$ and concentrated. The residue was purified by flash silica gel chromatography (EtOAc/hexane=1:10~1:3 as eluent) to give 2-[(4S)-2-[(1S)-1-benzoyloxypropyl]-5-oxo-1,3-oxathiolan-4-yl]acetic acid (compound 4a) 3.9 g as a brown oil.

Compound 4a: $^1$H NMR (400 MHz, DMSO-d$_6$) δ ppm: 12.78 (brs, 1H), 7.98 (m, 2H), 7.71 (m, 1H), 7.57 (t, J=7.7 Hz, 2H), 5.81-5.91 (m, 1H), 5.19-5.39 (m, 1H), 4.21-4.50 (m, 1H), 2.63-3.00 (m, 2H), 1.63-1.88 (m, 2H), 0.93 (t, J=7.4 Hz, 3H). MS obsd. (ESI$^+$) [(M+H)$^+$]: 325.

Preparation of [(1S)-1-[(4S)-4-(2-methoxy-2-oxo-ethyl)-5-oxo-1,3-oxathiolan-2-yl]propyl]benzoate (compound 4b)

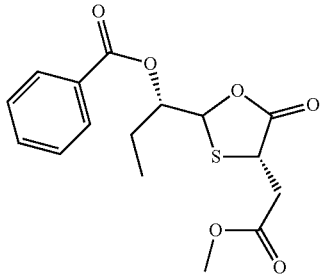 [SMILES: CC[C@H](OC(=O)c1ccccc1)C1OC(=O)[C@H](CC(=O)OC)S1]

To a solution of 2-((4S)-2-((S)-1-(benzoyloxy)propyl)-5-oxo-1,3-oxathiolan-4-yl)acetic acid (compound 4a) (3.6 g, 12 mmol) in Et$_2$O/MeOH (v/v=4:1, 100 mL) was added TMSCHN$_2$ (2 M in hexane, 8.3 mL, 17 mmol) at rt. Then the reaction mixture was stirred at rt for 2 h, then quenched with water (50 mL), extracted with EtOAc. The combined organic extract was washed with brine, dried over Na$_2$SO$_4$ and concentrated. The residue was purified by flash chromatography (EtOAc/hexane=1:10~1:1 as eluent) to give the [(1S)-1-[(4S)-4-(2-methoxy-2-oxo-ethyl)-5-oxo-1,3-oxathiolan-2-yl]propyl]benzoate (compound 4b) 3.6 g as a cis/trans mixture. [(1S)-1-[(4S)-4-(2-methoxy-2-oxo-ethyl)-5-oxo-1,3-oxathiolan-2-yl]propyl]benzoate (compound 4b) (2.1 g, 6.2 mmol) was further separated by SFC to give [(1S)-1-[(2S,4S)-4-(2-methoxy-2-oxo-ethyl)-5-oxo-1,3-oxathiolan-2-yl]propyl]benzoate (compound 4b1) 0.87 g and [(1S)-1-[(2R,4S)-4-(2-methoxy-2-oxo-ethyl)-5-oxo-1,3-oxathiolan-2-yl]propyl]benzoate (compound 4b2) 0.9 g as yellowish oils. The absolute configuration of compound 4b1 and compound 4b2 were determined by NOESY.

Compound 4b: $^1$H NMR (400 MHz, CD$_3$OD) δ ppm: 8.05 (m, 2H), 7.66 (m, 1H), 7.52 (m, 2H), 5.81 (m, 1H), 5.26-5.44 (m, 1H), 4.23-4.50 (m, 1H), 3.62-3.77 (m, 3H), 2.79-3.12 (m, 2H), 1.77-1.99 (m, 2H), 0.99-1.09 (m, 3H). MS obsd. (ESI$^+$) [(M+H)$^+$]: 339.

Compound 4b1: $^1$H NMR (400 MHz, CD$_3$OD) δ ppm: 8.05 (dd, J=8.3, 1.3 Hz, 2H), 7.67 (m, 1H), 7.53 (m, 2H), 5.80 (dd, J=4.3, 0.8 Hz, 1H), 5.31 (m, 1H), 4.27 (m, 1H), 3.70 (s, 3H), 3.06-2.92 (m, 2H), 1.91 (m, 2H), 1.03 (t, J=7.5 Hz, 3H).

Compound 4b2: $^1$H NMR (400 MHz, CD$_3$OD) δ ppm: 8.06 (dd, J=1.3, 8.3 Hz, 2H), 7.66 (m, 1H), 7.53 (m, 2H), 5.82 (d, J=4.8 Hz, 1H), 5.39 (td, J=8.8, 4.4 Hz, 1H), 4.47 (dd, J=8.5, 4.3 Hz, 1H), 3.73 (s, 3H), 3.07 (dd, J=17.2, 4.4 Hz, 1H), 2.91-2.80 (m, 1H), 2.00-1.77 (m, 2H), 1.03 (t, J=7.5 Hz, 3H).

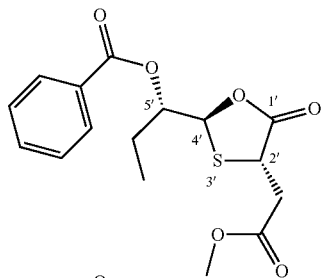

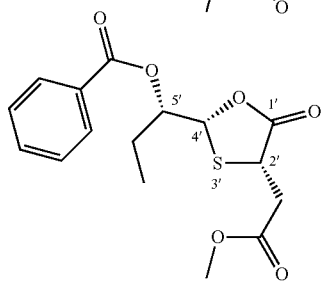

For compound 4b1, the NOESY correlation of C2'-H and C5'-H was observed. For compound 4b2, the NOESY correlation of C2'-H and C4'-H was observed.

Preparation of [(1S)-1-[(4S)-5-acetoxy-4-(2-methoxy-2-oxo-ethyl)-1,3-oxathiolan-2-yl]propyl]benzoate (compound 4c)

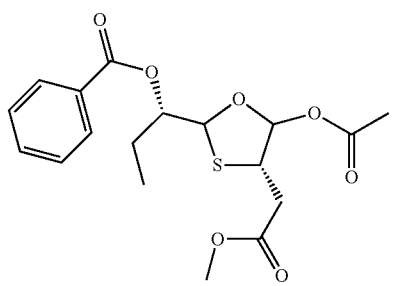 [SMILES: CC[C@H](OC(=O)c1ccccc1)C1OC(OC(C)=O)[C@H](CC(=O)OC)S1]

To a solution of [(1S)-1-[(4S)-4-(2-methoxy-2-oxo-ethyl)-5-oxo-1,3-oxathiolan-2-yl]propyl]benzoate (compound 4b) (3.3 g, 9.8 mmol in anhydrous THF (60 mL) was added LiAlH(Ot-Bu)₃ (1 M in THF, 14.6 mL, 15 mmol) dropwise at −78° C. The reaction mixture was warmed up and being stirred at rt for 2 h. Then pyridine (3.86 g, 3.9 mL, 49 mmol), acetic anhydride (4.98 g, 4.6 mL, 49 mmol) and DMAP (3.57 g, 29 mmol) were added. The reaction mixture was stirred at rt overnight and then quenched with saturated NH₄Cl. The solution was extracted with DCM (50 mL) three times. The combined organic layer was washed with brine, dried over Na₂SO₄ and concentrated. The residue was purified by flash silica gel chromatography (EtOAc/hexane=1:10~3:1 as eluent) to give [(1S)-1-[(4S)-5-acetoxy-4-(2-methoxy-2-oxo-ethyl)-1,3-oxathiolan-2-yl]propyl]benzoate (compound 4c) 3.7 g as a yellowish oil.

Compound 4c: ¹H NMR (400 MHz, CD₃OD) δ ppm: 8.05 (m, 2H), 7.64 (m, 1H), 7.51 (m, 2H), 6.34-6.50 (m, 1H), 5.42-5.67 (m, 1H), 5.23-5.36 (m, 1H), 3.83-4.16 (m, 1H), 3.64-3.73 (m, 3H), 2.59-2.92 (m, 2H), 2.01-2.38 (m, 3H), 1.57-1.93 (m, 2H), 0.92-1.04 (m, 3H). MS obsd. (ESI⁺) [(M+H)⁺]: 383.

Preparation of [(1S)-1-[(4S,5R)-5-(5-amino-2,7-dioxo-6H-thiazolo[4,5-d]pyrimidin-3-yl)-4-(2-methoxy-2-oxo-ethyl)-1,3-oxathiolan-2-yl]propyl]benzoate (compound 4d)

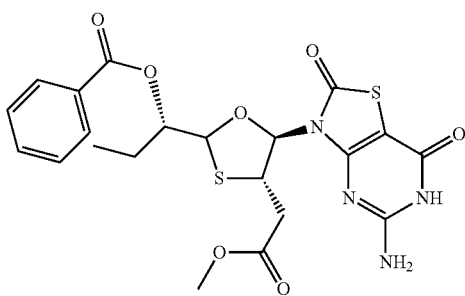 [SMILES: CC[C@H](OC(=O)c1ccccc1)C1O[C@@H](n2c(=O)sc3c(=O)[nH]c(N)nc32)[C@H](CC(=O)OC)S1]

To the solution of 5-amino-7-hydroxythiazolo[4,5-d]pyrimidin-2(3H)-one (1.4 g, 7.6 mmol) in anhydrous CH₃CN (50 mL) was added BSA (5.71 g, 28 mmol). The mixture was heated at 60° C. until the solution was clear. The solvent was removed under reduced pressure. The residue was re-dissolved in anhydrous DCM (100 mL). To the solution was added [(1S)-1-[(4S)-5-acetoxy-4-(2-methoxy-2-oxo-ethyl)-1,3-oxathiolan-2-yl]propyl]benzoate (compound 4c) (2.9 g, 7.6 mmol) and TMSI (3.34 g, 2.3 mL, 17 mmol). The reaction mixture was stirred at rt overnight and then quenched with saturated NaHCO₃. The solution was extracted with DCM (100 mL) three times and washed with saturated NaHCO₃ and brine. The organic layer was dried over Na₂SO₄ and then concentrated. The residue was purified by flash silica gel chromatography (DCM/MeOH=20:1 as eluent) to give [(1S)-1-[(4S,5R)-5-(5-amino-2,7-dioxo-6H-thiazolo[4,5-d]pyrimidin-3-yl)-4-(2-methoxy-2-oxo-ethyl)-1,3-oxathiolan-2-yl]propyl]benzoate (compound 4d) 1.7 g as a yellowish solid. MS obsd. (ESI⁺) [(M+H)⁺]: 507.

Preparation of methyl 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate (Example 4)

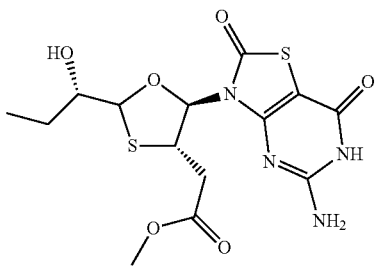 [SMILES: CC[C@H](O)C1O[C@@H](n2c(=O)sc3c(=O)[nH]c(N)nc32)[C@H](CC(=O)OC)S1]

To a solution of [(1S)-1-[(4S,5R)-5-(5-amino-2,7-dioxo-6H-thiazolo[4,5-d]pyrimidin-3-yl)-4-(2-methoxy-2-oxo-ethyl)-1,3-oxathiolan-2-yl]propyl]benzoate (compound 4d) (0.25 g, 0.49 mmol) in MeOH (10 mL) was added K₂CO₃ (0.13 g, 0.94 mmol). The mixture was stirred at rt overnight. After the reaction was completed, the reaction mixture was neutralized to pH 7 with HOAc. The mixture was concentrated in vacuo. The residue was purified by preparative HPLC to afford methyl 2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate (Example 4-P1) 3 mg and methyl 2-[(2R,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate (Example 4-P2) 4 mg as white powders. The absolute configuration of Example 4-P1 and Example 4-P2 were determined by NOESY.

Example 4-P1

¹H NMR (400 MHz, CD₃OD) δ ppm: 5.94 (d, J=8.5 Hz, 1H), 5.17 (d, J=5.3 Hz, 1H), 4.81 (m, 1H), 3.65 (ddd, J=8.9, 5.1, 3.5 Hz, 1H), 3.60 (s, 3H), 2.76 (d, J=7.0 Hz, 2H), 1.64 (m, 1H), 1.50 (m, 1H), 1.02 (t, J=7.4 Hz, 3H). MS obsd. (ESI⁺) [(M+H)⁺]: 403.

Example 4-P2

¹H NMR (400 MHz, CD₃OD) δ ppm: 6.14 (d, J=7.0 Hz, 1H), 5.67 (d, J=5.5 Hz, 1H), 4.79 (q, J=7.1 Hz, 1H), 3.68 (ddd, J=8.8, 5.2, 3.8 Hz, 1H), 3.61 (s, 3H), 2.81 (m, 2H), 1.66 (m, 1H), 1.41 (m, 1H), 1.01 (t, J=7.4 Hz, 3H). MS obsd. (ESI⁺) [(M+H)⁺]: 403.

Example 4-P1

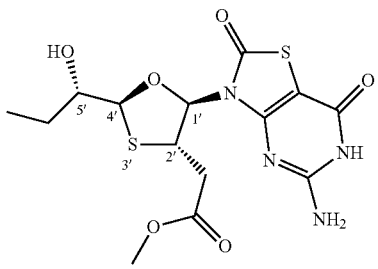

-continued

Example 4-P2

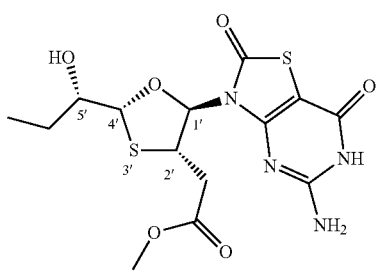

For Example 4-P1, the NOESY correlation of C2'-H and C5'-H, C1'-H and C4'-H were observed. For Example 4-P2, the NOESY correlation of C2'-H and C4'-H was observed, C1'-H was not correlated with C4'-H.

Example 5

2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid

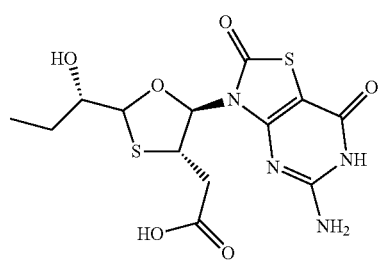 [SMILES: CC[C@H](O)C1O[C@@H](n2c(=O)sc3c(=O)[nH]c(N)nc32)[C@H](CC(=O)O)S1]

Preparation of 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid (Example 5)

To a crude methyl 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate (Example 4) (400 mg, 1.0 mmol) in THF (10 mL) was added aqueous LiOH (1 M, 5 mL, 5 mmol). The reaction mixture was stirred at rt for 2 h, then neutralized with 1N HCl to pH 7, and concentrated to give the crude product which was purified by preparative HPLC to afford 2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid (Example 5-P1) 3 mg and 2-[(2R,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid (Example 5-P2) 4 mg as white powders. The absolute configuration of Example 5-P1 and Example 5-P2 were determined by NOESY.

Example 5-P1

$^1$H NMR (400 MHz, CD$_3$OD) δ ppm: 5.93 (d, J=8.5 Hz, 1H), 5.14 (d, J=5.5 Hz, 1H), 4.82 (m, 1H), 3.65 (m, 1H), 2.63 (m, 2H), 1.64 (m, 1H), 1.49 (m, 1H), 1.02 (t, J=7.4 Hz, 3H). MS obsd. (ESI$^+$) [(M+H)$^+$]: 389.

Example 5-P2

$^1$H NMR (400 MHz, CD$_3$OD) δ ppm: 6.13 (d, J=7.0 Hz, 1H), 5.66 (d, J=5.5 Hz, 1H), 4.79 (m, 1H), 3.67 (ddd, J=8.9, 5.3, 3.6 Hz, 1H), 2.75 (m, 1H), 2.66 (m, 1H), 1.68 (m, 1H), 1.42 (m, 1H), 1.01 (t, J=7.4 Hz, 3H). MS obsd. (ESI$^+$) [(M+H)$^+$]: 389.

Example 5-P1

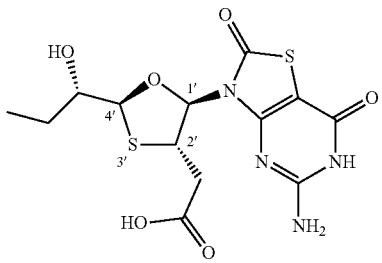

Example 5-P2

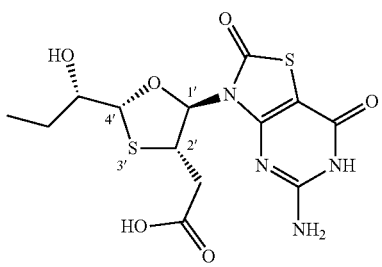

For Example 5-P1, NOESY correlation of C1'-H and C4'-H was observed, C2'-H was not correlated with C4'-H. For Example 5-P2, NOESY correlation of C2'-H and C4'-H was observed, C1'-H was not correlated with C4'-H.

Example 6

2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide

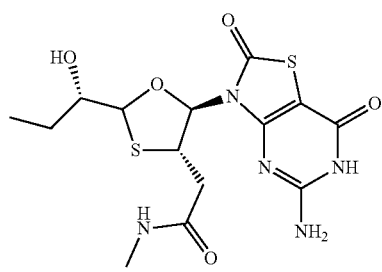 [SMILES: CC[C@H](O)C1O[C@@H](n2c(=O)sc3c(=O)[nH]c(N)nc32)[C@H](CC(=O)NC)S1]

Preparation of 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide (Example 6)

To the crude 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid (Example 5) (200 mg, 0.51 mmol) in DMF (5 mL) was added methylamine hydrochloride (70 mg, 1.03 mol), DIPEA (0.36 mL, 2.1 mmol) and HATU (294 mg, 0.77 mmol). The reaction was being stirred at rt for 2 h, then quenched with saturated NH$_4$Cl, and extracted with EtOAc. The organic layer was concentrated to give the crude product which was further purified by preparative HPLC to afford 2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide (Example 6-P1) 2 mg and 2-[(2R,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide (Example 6-P2) 5 mg as white powders. The absolute configuration was determined in analogy to the assignment of Example 5.

Example 6-P1

$^1$H NMR (400 MHz, CD$_3$OD) δ ppm: 5.91 (d, J=8.8 Hz, 1H), 5.15 (d, J=5.3 Hz, 1H), 4.84 (m, 1H), 3.65 (m, 1H), 2.62 (s, 3H), 2.55 (d, J=7.3 Hz, 2H), 1.64 (m, 1H), 1.50 (m, 1H), 1.02 (t, J=7.4 Hz, 3H). MS obsd. (ESI$^+$) [(M+H)$^+$]: 402.

Example 6-P2

$^1$H NMR (400 MHz, CD$_3$OD) δ ppm: 6.10 (d, J=7.3 Hz, 1H), 5.69 (d, J=5.5 Hz, 1H), 4.83 (m, 1H), 3.68 (m, 1H), 2.64 (s, 3H), 2.57 (m, 2H), 1.68 (m, 1H), 1.42 (m, 1H), 1.01 (t, J=7.4 Hz, 3H). MS obsd. (ESI$^+$) [(M+H)$^+$]: 402.

Example 7

2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide

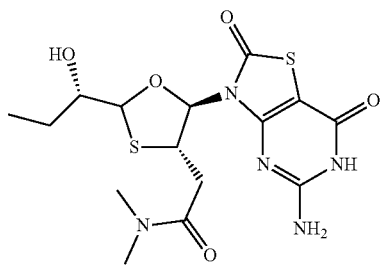 [SMILES: CC[C@H](O)C1O[C@@H](n2c(=O)sc3c(=O)[nH]c(N)nc32)[C@H](CC(=O)N(C)C)S1]

Preparation of 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide (7)

The title compound was prepared in analogy to Example 6, by using dimethylamine instead of methylamine hydrochloride. Example 7 was further purified by preparative HPLC to afford 2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide (Example 7-P1) 4 mg and 2-[(2R,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide (Example 7-P2) 9 mg as white powders. The absolute configuration of Example 7-P1 and Example 7-P2 were determined in analogy to the assignment of Example 5.

Example 7-P1

$^1$H NMR (400 MHz, CD$_3$OD) δ ppm: 5.93 (d, J=8.5 Hz, 1H), 5.14 (d, J=5.3 Hz, 1H), 4.91 (m, 1H), 3.66 (m, 1H), 3.04 (s, 3H), 2.89 (m, 1H), 2.84 (s, 3H), 2.77 (m, 1H), 1.65 (m, 1H), 1.50 (m, 1H), 1.02 (t, J=7.4 Hz, 3H). MS obsd. (ESI$^+$) [(M+H)$^+$]: 416.

Example 7-P2

$^1$H NMR (400 MHz, CD$_3$OD) δ ppm: 6.14 (d, J=7.0 Hz, 1H), 5.65 (d, J=5.0 Hz, 1H), 4.84 (m, 1H), 3.69 (ddd, J=8.8, 5.0, 3.8 Hz, 1H), 3.06 (s, 3H), 2.94 (m, 1H), 2.82 (m, 4H), 1.67 (m, 1H), 1.41 (m, 1H), 1.01 (t, J=7.4 Hz, 3H). MS obsd. (ESI$^+$) [(M+H)$^+$]: 416.

Example 8

5-Amino-3-[(4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione

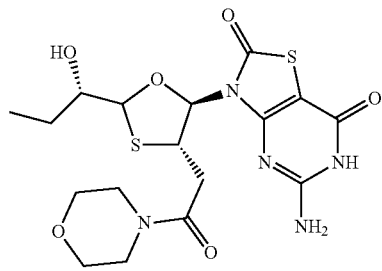 [SMILES: CC[C@H](O)C1O[C@@H](n2c(=O)sc3c(=O)[nH]c(N)nc32)[C@H](CC(=O)N2CCOCC2)S1]

Preparation of 5-amino-3-[(4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione (compound 8)

The title compound was prepared in analogy to Example 6, by using morpholine instead of methylamine hydrochloride. Example 8 was further purified by preparative HPLC to afford 5-amino-3-[(2S,4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione (Example 8-P1) 4 mg and 5-amino-3-[(2R,4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione (Example 8-P2) 10 mg as white powders. The absolute configuration of Example 8-P1 and Example 8-P2 were determined in analogy to the assignment of Example 5.

Example 8-P1

$^1$H NMR (400 MHz, CD$_3$OD) δ ppm: 5.93 (d, J=8.5 Hz, 1H), 5.14 (d, J=5.3 Hz, 1H), 4.94 (m, 1H), 3.65 (m, 3H), 3.59 (m, 2H), 3.48 (m, 4H), 2.84 (m, 2H), 1.65 (m, 1H), 1.50 (m, 1H), 1.02 (t, J=7.4 Hz, 3H). MS obsd. (ESI$^+$) [(M+H)$^+$]: 458.

Example 8-P2

$^1$H NMR (400 MHz, CD$_3$OD) δ ppm: 6.13 (m, 1H), 5.65 (d, J=5.0 Hz, 1H), 4.93 (m, 1H), 3.68 (m, 3H), 3.60 (m, 2H), 3.52 (m, 2H), 3.48 (m, 2H), 2.92 (m, 2H), 2.86 (m, 1H), 1.67 (m, 1H), 1.41 (m, 1H), 1.01 (m, 3H). MS obsd. (ESI$^+$) [(M+H)$^+$]: 458.

Example 9

Methyl 2-[5-(5-amino-2,7-dioxo-6H-thiazolo[4,5-d]pyrimidin-3-yl)-2-[(1S)-1-hydroxyethyl]-1,3-oxa-thiolan-4-yl]acetate

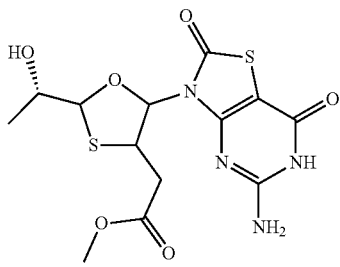 [SMILES: COC(=O)CC1SC([C@H](C)O)OC1n1c(=O)sc2c(=O)[nH]c(N)nc21]

Preparation of [(1S)-1-methyl-2-oxo-ethyl]benzoate (compound 9a)

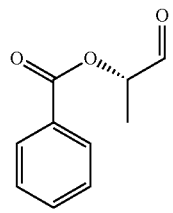

A mixture of propionaldehyde (5.0 g, 86 mmol), [diphenyl-[(2S)-pyrrolidin-2-yl]methoxy]-trimethyl-silane (2.8 g, 8.6 mmol) and hydroquinone (948 mg, 8.6 mmol) in THF (200 mL) was stirred at 0° C. Then to the mixture was added benzyl peroxide (22.9 g, 95 mmol). After being stirred for 4 h at 0° C. to rt, the reaction mixture was poured into aqueous 1N HCl (200 mL) and extracted with EtOAc, washed with saturated NaHCO$_3$ and brine, dried over Na$_2$SO$_4$, and concentrated. The residue was purified by flash silica gel chromatography (EtOAc/hexane=1:10~1:3 as eluent) to afford [(1S)-1-methyl-2-oxo-ethyl]benzoate (compound 9a) 4.5 g as a yellowish oil.

Compound 9a: $^1$H NMR (400 MHz, DMSO-d$_6$) δ ppm: 9.64 (m, 1H), 8.03 (m, 2H), 7.71 (m, 1H), 7.62 (m, 2H), 4.99 (m, 1H), 1.48 (m, 3H). MS obsd. (ESI$^+$) [(M+H)$^+$]: 179.

Preparation of 2-[2-[(1S)-1-benzoyloxyethyl]-5-oxo-1,3-oxathiolan-4-yl]acetic acid (compound 9b)

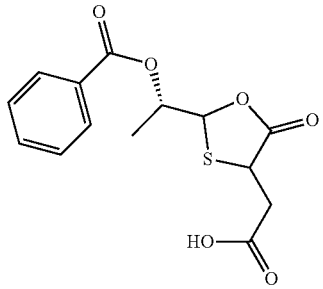 [SMILES: C[C@H](OC(=O)c1ccccc1)C1OC(=O)C(CC(=O)O)S1]

A mixture of [(1S)-1-methyl-2-oxo-ethyl]benzoate (compound 9a) (3.0 g, 17 mmol), 2-mercaptosuccinic acid (2.53 g, 17 mmol) and p-TsOH (320 mg, 1.7 mmol) in toluene (150 mL) was stirred at 60° C. for 4 h. After the reaction was completed, the reaction mixture was diluted with EtOAc (50 mL), washed with saturated NaHCO$_3$ and brine, dried over Na$_2$SO$_4$ and concentrated. The residue was purified by flash silica gel chromatography (EtOAc/hexane=1:10~1:3 as eluent) to give 2-[2-[(1S)-1-benzoyloxyethyl]-5-oxo-1,3-oxathiolan-4-yl]acetic acid (compound 9b) 4.7 g as a yellowish oil.

Compound 9b: $^1$H NMR (400 MHz, DMSO-d$_6$) δ ppm: 12.76 (brs, 1H), 7.95 (m, 2H), 7.70 (m, 1H), 7.56 (t, J=7.7, 2H), 5.78-5.86 (m, 1H), 5.24-5.40 (m, 1H), 4.28-4.54 (m, 1H), 2.57-3.02 (m, 2H), 1.33-1.42 (m, 3H). MS obsd. (ESI$^+$) [(M+H)$^+$]: 311.

Preparation of [(1S)-1-[4-(2-methoxy-2-oxo-ethyl)-5-oxo-1,3-oxathiolan-2-yl]ethyl]benzoate (compound 9c)

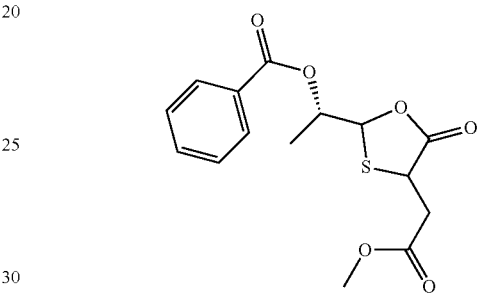

To a solution of 2-[2-[(1S)-1-benzoyloxyethyl]-5-oxo-1,3-oxathiolan-4-yl]acetic acid (compound 9b) (1.7 g, 5.5 mmol) in Et$_2$O/MeOH (v/v=4:1, 50 mL) was added TMSCHN$_2$ (2 M in hexane, 4.1 mL, 8.2 mmol) at rt. The reaction mixture was stirred at rt for 2 h, then quenched with water (50 mL), extracted with EtOAc. The combined organic extract was washed with brine, dried over Na$_2$SO$_4$ and concentrated. The residue was purified by flash silica gel chromatography (EtOAc/hexane=1:10~1:1 as eluent) to afford [(1S)-1-[4-(2-methoxy-2-oxo-ethyl)-5-oxo-1,3-oxa-thiolan-2-yl]ethyl]benzoate (compound 9c) 1.5 g as a yellowish oil.

Compound 9c: $^1$H NMR (400 MHz, DMSO-d$_6$) δ ppm: 7.96 (m, 2H), 7.71 (m, 1H), 7.57 (t, J=7.7 Hz, 2H), 5.77-5.90 (m, 1H), 5.21-5.44 (m, 1H), 4.34-4.59 (m, 1H), 3.55-3.67 (m, 3H), 2.74-3.09 (m, 2H), 1.38 (q, J=6.4 Hz, 3H). MS obsd. (ESI$^+$) [(M+H)$^+$]: 325.

Preparation of [(1S)-1-[5-acetoxy-4-(2-methoxy-2-oxo-ethyl)-1,3-oxathiolan-2-yl]ethyl]benzoate (compound 9d)

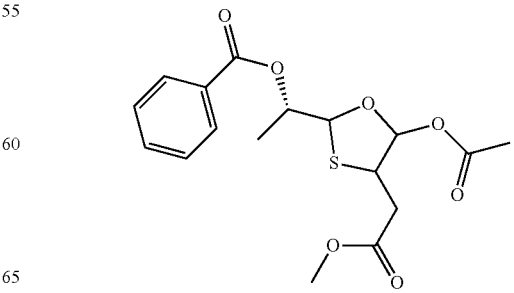

To a solution of [(1S)-1-[4-(2-methoxy-2-oxo-ethyl)-5-oxo-1,3-oxathiolan-2-yl]ethyl]benzoate (compound 9c) (1.5 g, 4.6 mmol) in anhydrous THF (60 mL) was added LiAlH(Ot-Bu)₃ (1 M in THF, 6.9 mL, 6.9 mmol) dropwise at −78° C. The reaction mixture was warmed up and being stirred at rt for 2 h. Then pyridine (1.87 mL, 23 mmol), acetic anhydride (2.2 mL, 23 mmol) and DMAP (1.69 g, 14 mmol) were added. The reaction mixture was stirred at rt overnight and then quenched with saturated NH₄Cl. The solution was extracted with DCM (50 mL) three times. The combined organic layer was washed with brine, dried over Na₂SO₄ and concentrated. The residue was purified by flash silica gel chromatography (EtOAc/hexane=1:10~1:3 as eluent) to afford [(1S)-1-[5-acetoxy-4-(2-methoxy-2-oxo-ethyl)-1,3-oxathiolan-2-yl]ethyl]benzoate (compound 9d) 1.1 g as a yellowish oil.

Compound 9d: ¹H NMR (400 MHz, CD₃OD) δ ppm: 8.03 (m, 2H), 7.63 (m, 1H), 7.50 (m, 2H), 6.36-6.54 (m, 1H), 5.43-5.60 (m, 1H), 5.22-5.42 (m, 1H), 3.85-4.16 (m, 1H), 3.67-3.75 (m, 3H), 2.58-2.95 (m, 2H), 1.94-2.15 (m, 3H), 1.29-1.47 (m, 3H). MS obsd. (ESI⁺) [(M+H)⁺]: 369.

Preparation of [(1S)-1-[5-(5-amino-2,7-dioxo-6H-thiazolo[4,5-d]pyrimidin-3-yl)-4-(2-methoxy-2-oxo-ethyl)-1,3-oxathiolan-2-yl]ethyl]benzoate (compound 9e)

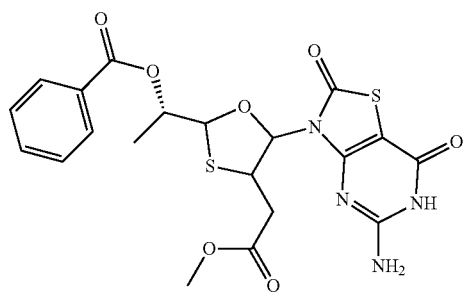 [SMILES: COC(=O)CC1SC([C@H](C)OC(=O)c2ccccc2)OC1n1c(=O)sc2c(=O)[nH]c(N)nc21]

To the solution of 5-amino-7-hydroxythiazolo[4,5-d]pyrimidin-2(3H)-one (550 mg, 3.0 mmol) in anhydrous ACN (50 mL) was added BSA (2.7 mL, 11 mmol). The mixture was heated at 60° C. until the solution was clear. Solvent was removed and the residue was re-dissolved in anhydrous DCM (100 mL). To the solution was added [(1S)-1-[5-acetoxy-4-(2-methoxy-2-oxo-ethyl)-1,3-oxathiolan-2-yl]ethyl]benzoate (compound 9d) (1.1 g, 3.0 mmol) and TMSI (0.91 mL, 6.6 mmol). The reaction mixture was stirred at rt overnight and then quenched with saturated NaHCO₃. The solution was extracted with DCM (100 mL) three times and washed with saturated NaHCO₃ and brine. The organic layer was dried over Na₂SO₄ and concentrated. The residue was purified by flash silica gel chromatography (DCM/methanol=20:1 as eluent) to afford [(1S)-1-[5-(5-amino-2,7-dioxo-6H-thiazolo[4,5-d]pyrimidin-3-yl)-4-(2-methoxy-2-oxo-ethyl)-1,3-oxathiolan-2-yl]ethyl]benzoate (compound 9e) 600 mg as a yellowish solid. MS obsd. (ESI⁺) [(M+H)⁺]: 493.

Preparation of methyl 2-[5-(5-amino-2,7-dioxo-6H-thiazolo[4,5-d]pyrimidin-3-yl)-2-[(1S)-1-hydroxy-ethyl]-1,3-oxathiolan-4-yl]acetate (Example 9)

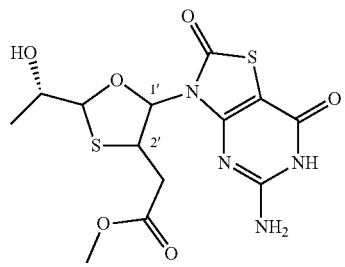 [SMILES: COC(=O)CC1SC([C@H](C)O)OC1n1c(=O)sc2c(=O)[nH]c(N)nc21]

To a solution of [(1S)-1-[5-(5-amino-2,7-dioxo-6H-thiazolo[4,5-d]pyrimidin-3-yl)-4-(2-methoxy-2-oxo-ethyl)-1,3-oxathiolan-2-yl]ethyl]benzoate (compound 9e) (0.6 g, 1.2 mmol) in MeOH (10 mL) was added K₂CO₃ (253 mg, 1.8 mmol). After being stirred at rt overnight, the reaction mixture was quenched with aqueous 1N HCl to pH 7, then concentrated to give the crude product which was further purified by preparative HPLC to afford Example 9-P1 (trans-1',2'-diastereomer 1) 8 mg, Example 9-P2 (trans-1',2'-diastereomer 2) 5 mg, Example 9-P3 (trans-1',2'-diastereomer 3) 2 mg and Example 9-P4 (trans-1',2'-diastereomer 4) 2.5 mg as white powders.

Example 9-P1

¹H NMR (400 MHz, CD₃OD) δ ppm: 6.14 (d, J=7.0 Hz, 1H), 5.62 (d, J=5.3 Hz, 1H), 4.80 (q, J=7.3 Hz, 1H), 3.92 (m, 1H), 3.61 (s, 3H), 2.82 (m, 2H), 1.23 (d, J=6.3 Hz, 3H). MS obsd. (ESI⁺) [(M+H)⁺]: 389.

Example 9-P2

¹H NMR (400 MHz, CD₃OD) δ ppm: 6.14 (d, J=7.0 Hz, 1H), 5.60 (d, J=6.0 Hz, 1H), 4.83 (q, J=7.3 Hz, 1H), 3.89 (quin, J=6.3 Hz, 1H), 3.61 (s, 3H), 2.81 (m, 2H), 1.21 (d, J=6.5 Hz, 3H). MS obsd. (ESI⁺) [(M+H)⁺]: 389.

Example 9-P3

¹H NMR (400 MHz, CD₃OD) δ ppm: 5.94 (d, J=8.5 Hz, 1H), 5.11 (d, J=5.8 Hz, 1H), 4.83 (m, 1H), 3.98 (m, 1H), 3.61 (s, 3H), 2.76 (d, J=7.3 Hz, 2H), 1.23 (d, J=6.3 Hz, 3H). MS obsd. (ESI⁺) [(M+H)⁺]: 389.

Example 9-P4

¹H NMR (400 MHz, CD₃OD) δ ppm: 5.95 (d, J=8.5 Hz, 1H), 5.14 (d, J=4.3 Hz, 1H), 4.75 (m, 1H), 4.02 (dd, J=6.4, 4.1 Hz, 1H), 3.60 (s, 3H), 2.75 (d, J=7.0 Hz, 2H), 1.21 (d, J=6.5 Hz, 3H). MS obsd. (ESI⁺) [(M+H)⁺]: 389.

Example 10

2-[5-(5-Amino-2,7-dioxo-6H-thiazolo[4,5-d]pyrimidin-3-yl)-2-[(1S)-1-hydroxyethyl]-1,3-oxathiolan-4-yl]acetic acid

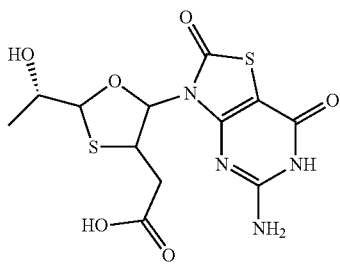

Preparation of 2-[5-(5-amino-2,7-dioxo-6H-thiazolo[4,5-d]pyrimidin-3-yl)-2-[(1S)-1-hydroxyethyl]-1,3-oxathiolan-4-yl]acetic acid (Example 10)

To a crude mixture of methyl 2-[5-(5-amino-2,7-dioxo-6H-thiazolo[4,5-d]pyrimidin-3-yl)-2-[(1S)-1-hydroxyethyl]-1,3-oxathiolan-4-yl]acetate Example 9 (280 mg, 0.72 mmol) in THF (10 mL) was added aqueous LiOH (1 M, 5 mL, 5.0 mmol). After being stirred at rt for 2 h, the reaction mixture was quenched with aqueous HCl to pH 6-7, then concentrated. The residue was purified by preparative HPLC to afford Example 10-P1 (trans-1',2'-diastereomer 1) 23 mg, Example 10-P2 (trans-1',2'-diastereomer 2) 20 mg, Example 10-P3 (trans-1',2'-diastereomer 3) 9 mg and Example 10-P4 (trans-1',2'-diastereomer 4) 9 mg as white powders.

(Example 10)

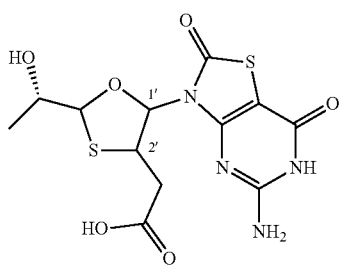 [SMILES: C[C@H](O)C1OC(n2c(=O)sc3c(=O)[nH]c(N)nc32)C(CC(=O)O)S1]

Example 10-P1

$^1$H NMR (400 MHz, CD$_3$OD) δ ppm: 6.12 (d, J=7.0 Hz, 1H), 5.57 (d, J=6.3 Hz, 1H), 4.83 (m, 1H), 3.88 (quin, J=6.3 Hz, 1H), 2.73 (m, 1H), 2.61 (m, 1H), 1.20 (d, J=6.3 Hz, 3H). MS obsd. (ESI$^+$) [(M+H)$^+$]: 375.

Example 10-P2

$^1$H NMR (400 MHz, CD$_3$OD) δ ppm: 6.13 (d, J=7.0 Hz, 1H), 5.60 (d, J=5.0 Hz, 1H), 4.80 (m, 1H), 3.91 (m, 1H), 2.74 (m, 1H), 2.65 (m, 1H), 1.24 (d, J=6.5 Hz, 3H). MS obsd. (ESI$^+$) [(M+H)$^+$]: 375.

Example 10-P3

$^1$H NMR (400 MHz, CD$_3$OD) δ ppm: 5.94 (d, J=8.5 Hz, 1H), 5.10 (d, J=5.8 Hz, 1H), 4.83 (m, 1H), 3.97 (quin, J=6.3 Hz, 1H), 2.68 (m, 2H), 1.23 (d, J=6.3 Hz, 3H). MS obsd. (ESI$^+$) [(M+H)$^+$]: 375.

Example 10-P4

$^1$H NMR (400 MHz, CD$_3$OD) δ ppm: 5.95 (d, J=8.8 Hz, 1H), 5.13 (d, J=4.3 Hz, 1H), 4.74 (m, 1H), 4.02 (m, 1H), 2.67 (m, 2H), 1.21 (d, J=6.3 Hz, 3H). MS obsd. (ESI$^+$) [(M+H)$^+$]: 375.

Example 11

2-[5-(5-Amino-2,7-dioxo-6H-thiazolo[4,5-d]pyrimidin-3-yl)-2-[(1S)-1-hydroxypentyl]-1,3-oxathiolan-4-yl]acetic acid

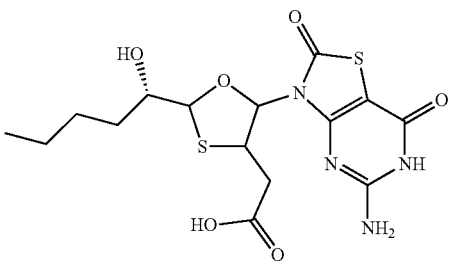 [SMILES: CCCC[C@H](O)C1OC(n2c(=O)sc3c(=O)[nH]c(N)nc32)C(CC(=O)O)S1]

Preparation of 2-[5-(5-amino-2,7-dioxo-6H-thiazolo[4,5-d]pyrimidin-3-yl)-2-[(1S)-1-hydroxypentyl]-1,3-oxathiolan-4-yl]acetic acid (Example 11)

The title compound was prepared in analogy to Example 10, by using hexanaldehyde instead of propionaldehyde. Example 11 was further purified by preparative HPLC to afford Example 11-P1 (trans-1',2'-diastereomer 1) 13 mg, Example 11-P2 (trans-1',2'-diastereomer 2) 21 mg, Example 11-P3 (trans-1',2'-diastereomer 3) 10 mg and Example 11-P4 (trans-1',2'-diastereomer 4) 18 mg as white powders.

(Example 11)

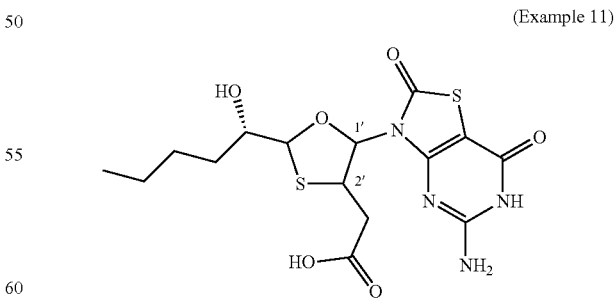

Example 11-P1

$^1$H NMR (400 MHz, CD$_3$OD) δ ppm: 6.10 (d, J=7.0 Hz, 1H), 5.61 (d, J=6.3 Hz, 1H), 4.84 (m, 1H), 3.66 (m, 1H), 2.65 (dd, J=15.1, 5.8 Hz, 1H), 2.48 (dd, J=15.3, 9.3 Hz, 1H), 1.50 (m, 3H), 1.39 (m, 3H), 0.94 (t, J=7.2 Hz, 3H). MS obsd. (ESI⁺) [(M+H)⁺]: 417.

Example 11-P2

¹H NMR (400 MHz, CD₃OD) δ ppm: 6.10 (d, J=7.3 Hz, 1H), 5.64 (d, J=5.3 Hz, 1H), 4.80 (dt, J=8.8, 6.5 Hz, 1H), 3.73 (m, 1H), 2.64 (dd, J=14.9, 5.6 Hz, 1H), 2.47 (dd, J=14.8, 9.0 Hz, 1H), 1.65 (m, 1H), 1.51 (m, 1H), 1.38 (m, 4H), 0.94 (t, J=7.2 Hz, 3H). MS obsd. (ESI⁺) [(M+H)⁺]: 417.

Example 11-P3

¹H NMR (400 MHz, CD₃OD) δ ppm: 5.90 (d, J=8.8 Hz, 1H), 5.09 (d, J=5.8 Hz, 1H), 4.83 (m, 1H), 3.72 (m, 1H), 2.58 (m, 1H), 2.45 (dd, J=15.6, 9.3 Hz, 1H), 1.59 (m, 1H), 1.51 (m, 1H), 1.38 (m, 4H), 0.94 (t, J=7.2 Hz, 3H). MS obsd. (ESI⁺) [(M+H)⁺]: 417.

Example 11-P4

¹H NMR (400 MHz, CD₃OD) δ ppm: 5.91 (d, J=8.8 Hz, 1H), 5.14 (d, J=4.3 Hz, 1H), 4.75 (td, J=9.0, 5.1 Hz, 1H), 3.85 (m, 1H), 2.55 (m, 1H), 2.41 (dd, J=15.1, 9.0 Hz, 1H), 1.46 (m, 6H), 0.94 (t, J=7.2 Hz, 3H). MS obsd. (ESI⁺) [(M+H)⁺]: 417.

Example 12

2-[5-(5-Amino-2,7-dioxo-6H-thiazolo[4,5-d]pyrimidin-3-yl)-2-[(1S)-1-hydroxybut-3-enyl]-1,3-oxathiolan-4-yl]acetic acid

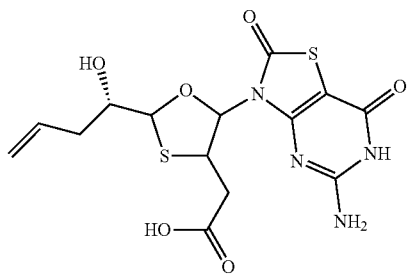 [SMILES: C=CC[C@H](O)C1OC(n2c(=O)sc3c(=O)[nH]c(N)nc32)C(CC(=O)O)S1]

Preparation of 2-[5-(5-amino-2,7-dioxo-6H-thiazolo[4,5-d]pyrimidin-3-yl)-2-[(1S)-1-hydroxybut-3-enyl]-1,3-oxathiolan-4-yl]acetic acid (12)

The title compound was prepared in analogy to Example 10, by using 4-methylhex-5-enal instead of propionaldehyde. Example 12 was further purified by preparative HPLC to afford Example 12-P1 (trans-1',2'-diastereomer 1) 23 mg, Example 12-P2 (trans-1',2'-diastereomer 2) 22 mg, Example 12-P3 (trans-1',2'-diastereomer 3) 16 mg and Example 12-P4 (trans-1',2'-diastereomer 4) 28 mg as white powders.

(Example 12)

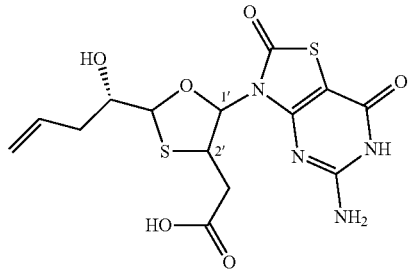

Example 12-P1

¹H NMR (400 MHz, CD₃OD) δ ppm: 6.13 (d, J=6.8 Hz, 1H), 5.91 (ddt, J=17.0, 10.1, 7.0 Hz, 1H), 5.65 (d, J=5.5 Hz, 1H), 5.10 (m, 2H), 4.83 (m, 1H), 3.74 (m, 1H), 2.73 (m, 1H), 2.63 (m, 1H), 2.31 (m, 2H). MS obsd. (ESI⁺) [(M+H)⁺]: 401.

Example 12-P2

¹H NMR (400 MHz, CD₃OD) δ ppm: 6.11 (d, J=7.0 Hz, 1H), 5.90 (ddt, J=17.2, 10.1, 6.9 Hz, 1H), 5.65 (d, J=5.5 Hz, 1H), 5.10 (m, 2H), 4.80 (m, 1H), 3.78 (m, 1H), 2.64 (dd, J=14.7, 5.6 Hz, 1H), 2.44 (m, 2H), 2.22 (m, 1H). MS obsd. (ESI⁺) [(M+H)⁺]: 401.

Example 12-P3

¹H NMR (400 MHz, CD₃OD) δ ppm: 5.93 (m, 2H), 5.10 (m, 3H), 4.83 (m, 1H), 3.81 (m, 1H), 2.56 (m, 1H), 2.42 (m, 2H), 2.30 (m, 1H). MS obsd. (ESI⁺) [(M+H)⁺]: 401.

Example 12-P4

¹H NMR (400 MHz, CD₃OD) δ ppm: 5.89 (m, 2H), 5.17 (d, J=4.3 Hz, 1H), 5.04-5.16 (m, 2H), 4.75 (m, 1H), 3.94 (m, 1H), 2.56 (m, 2H), 2.31 (m, 2H). MS obsd. (ESI⁺) [(M+H)⁺]: 401.

Example 13

Methyl 2-[5-(5-amino-2,7-dioxo-6H-thiazolo[4,5-d]pyrimidin-3-yl)-2-[(S)-cyclopropyl(hydroxy)methyl]-1,3-oxathiolan-4-yl]acetate

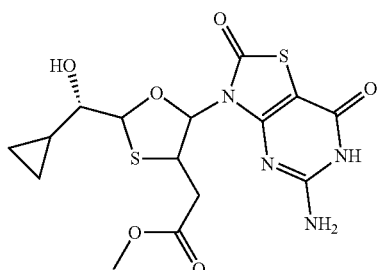

Preparation of methyl 2-[5-(5-amino-2,7-dioxo-6H-thiazolo[4,5-d]pyrimidin-3-yl)-2-[(S)-cyclopropyl(hydroxy)methyl]-1,3-oxathiolan-4-yl]acetate (Example 13)

The title compound was prepared in analogy to Example 9, by using 2-cyclopropylacetaldehyde instead of propionaldehyde. Example 13 was further purified by preparative HPLC to afford Example 13-P1 (trans-1',2'-diastereomer 1) 11 mg, Example 13-P2 (trans-1',2'-diastereomer 2) 8 mg, Example 13-P3 (trans-1',2'-diastereomer 3) 7 mg and Example 13-P4 (trans-1',2'-diastereomer 4) 6 mg as white powders.

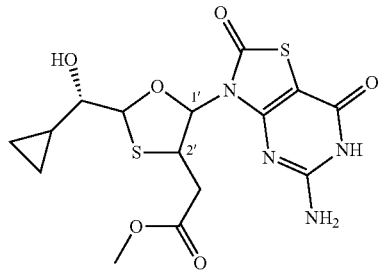 [SMILES: COC(=O)CC1SC([C@@H](O)C2CC2)OC1n1c(=O)sc2c(=O)[nH]c(N)nc21]

(Example 13)

Example 13-P1

$^1$H NMR (400 MHz, CD$_3$OD) δ ppm: 6.17 (d, J=7.0 Hz, 1H), 5.76 (d, J=4.8 Hz, 1H), 4.80 (q, J=7.0 Hz, 1H), 3.61 (s, 3H), 3.27 (dd, J=7.5, 4.8 Hz, 1H), 2.83 (dd, J=7.3, 1.0 Hz, 2H), 0.90 (m, 1H), 0.52 (m, 2H), 0.39 (m, 2H). MS obsd. (ESI$^+$) [(M+H)$^+$]: 415.

Example 13-P2

$^1$H NMR (400 MHz, CD$_3$OD) δ ppm: 6.15 (d, J=7.0 Hz, 1H), 5.77 (d, J=6.3 Hz, 1H), 4.83 (m, 1H), 3.61 (s, 3H), 3.02 (dd, J=8.5, 6.3 Hz, 1H), 2.81 (m, 2H), 0.98 (m, 1H), 0.56 (m, 2H), 0.42 (m, 2H). MS obsd. (ESI$^+$) [(M+H)$^+$]: 415.

Example 13-P3

$^1$H NMR (400 MHz, CD$_3$OD) δ ppm: 5.95 (d, J=8.3 Hz, 1H), 5.26 (d, J=5.5 Hz, 1H), 4.83 (m, 1H), 3.61 (s, 3H), 3.15 (dd, J=8.0, 5.5 Hz, 1H), 2.78 (d, J=7.0 Hz, 2H), 0.96 (m, 1H), 0.54 (m, 2H), 0.46 (m, 1H), 0.39 (m, 1H). MS obsd. (ESI$^+$) [(M+H)$^+$]: 415.

Example 13-P4

$^1$H NMR (400 MHz, CD$_3$OD) δ ppm: 5.96 (d, J=8.5 Hz, 1H), 5.33 (d, J=4.0 Hz, 1H), 4.74 (m, 1H), 3.60 (s, 3H), 3.27 (dd, J=8.0, 3.8 Hz, 1H), 2.76 (d, J=7.0 Hz, 2H), 0.92 (m, 1H), 0.52 (m, 2H), 0.42 (m, 2H), 0.35 (m, 1H). MS obsd. (ESI$^+$) [(M+H)$^+$]: 415.

Example 14

2-[5-(5-Amino-2,7-dioxo-6H-thiazolo[4,5-d]pyrimidin-3-yl)-2-[(S)-cyclopropyl(hydroxy)methyl]-1,3-oxathiolan-4-yl]acetic acid

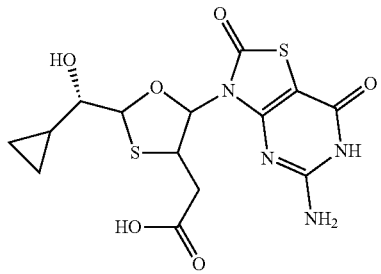

Preparation of 2-[5-(5-amino-2,7-dioxo-6H-thiazolo[4,5-d]pyrimidin-3-yl)-2-[(S)-cyclopropyl(hydroxy)methyl]-1,3-oxathiolan-4-yl]acetic acid (Example 14)

The title compound was prepared in analogy to Example 10, by using 2-cyclopropylacetaldehyde instead of propionaldehyde. Example 14 was further purified by preparative HPLC to afford Example 14-P1 (trans-1',2'-diastereomer 1) 49 mg, Example 14-P2 (trans-1',2'-diastereomer 2) 38 mg, Example 14-P3 (trans-1',2'-diastereomer 3) 12 mg and Example 14-P4 (trans-1',2'-diastereomer 4) 15 mg as white powders.

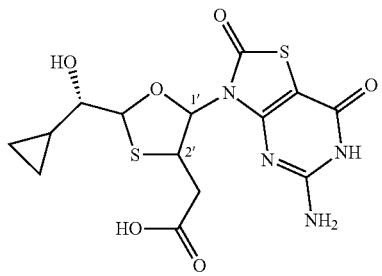 [SMILES: Nc1nc2c(sc(=O)n2C2OC([C@@H](O)C3CC3)SC2CC(=O)O)c(=O)[nH]1]

(Example 14)

Example 14-P1

$^1$H NMR (400 MHz, CD$_3$OD) δ ppm: 6.16 (d, J=7.0 Hz, 1H), 5.75 (d, J=6.3 Hz, 1H), 4.83 (m, 1H), 3.02 (dd, J=8.5, 6.3 Hz, 1H), 2.75 (m, 2H), 0.99 (m, 1H), 0.56 (m, 2H), 0.41 (m, 2H). MS obsd. (ESI$^+$) [(M+H)$^+$]: 401.

Example 14-P2

$^1$H NMR (400 MHz, CD$_3$OD) δ ppm: 6.18 (d, J=7.0 Hz, 1H), 5.75 (d, J=4.8 Hz, 1H), 4.80 (q, J=7.1 Hz, 1H), 3.27 (dd, J=7.5, 4.8 Hz, 1H), 2.77 (m, 2H), 0.90 (m, 1H), 0.52 (m, 2H), 0.39 (m, 2H). MS obsd. (ESI$^+$) [(M+H)$^+$]: 401.

Example 14-P3

$^1$H NMR (400 MHz, CD$_3$OD) δ ppm: 5.95 (d, J=8.3 Hz, 1H), 5.26 (d, J=5.8 Hz, 1H), 4.82 (m, 1H), 3.15 (dd, J=8.0, 5.8 Hz, 1H), 2.71 (m, 2H), 0.96 (m, 1H), 0.53 (m, 2H), 0.46 (m, 1H), 0.40 (m, 1H). MS obsd. (ESI$^+$) [(M+H)$^+$]: 401.

Example 14-P4

¹H NMR (400 MHz, CD₃OD) δ ppm: 5.97 (d, J=8.5 Hz, 1H), 5.33 (d, J=4.0 Hz, 1H), 4.73 (m, 1H), 3.27 (dd, J=8.0, 3.8 Hz, 1H), 2.71 (d, J=6.8 Hz, 2H), 0.93 (m, 1H), 0.53 (m, 2H), 0.43 (m, 1H), 0.35 (m, 1H). MS obsd. (ESI⁺) [(M+H)⁺]: 401.

Example 15

[(1S)-1-[(2S,4S,5R)-5-(5-amino-2-oxo-thiazolo[4,5-d]pyrimidin-3-yl)-4-(2-methoxy-2-oxo-ethyl)-1,3-oxathiolan-2-yl]propyl]benzoate

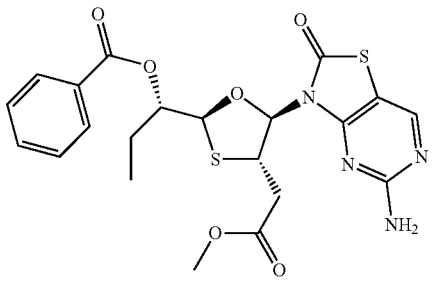 [SMILES: CC[C@H](OC(=O)c1ccccc1)[C@H]1O[C@@H](n2c(=O)sc3cnc(N)nc32)[C@H](CC(=O)OC)S1]

Preparation of [(1S)-1-[(2S,4S,5R)-5-(5-amino-2-oxo-thiazolo[4,5-d]pyrimidin-3-yl)-4-(2-methoxy-2-oxo-ethyl)-1,3-oxathiolan-2-yl]propyl]benzoate (Example 15)

The title compound 400 mg was prepared as white powder in analogy to [(1S)-1-[(4S,5R)-5-(5-amino-2,7-dioxo-6H-thiazolo[4,5-d]pyrimidin-3-yl)-4-(2-methoxy-2-oxo-ethyl)-1,3-oxathiolan-2-yl]propyl]benzoate (compound 4d), by using [(1S)-1-[(2S,4S)-4-(2-methoxy-2-oxo-ethyl)-5-oxo-1,3-oxathiolan-2-yl]propyl]benzoate (compound 4b1) and 5-amino-3H-thiazolo[4,5-d]pyrimidin-2-one instead of [(1S)-1-[(4S)-4-(2-methoxy-2-oxo-ethyl)-5-oxo-1,3-oxathiolan-2-yl]propyl]benzoate (compound 4b) and 5-amino-3,7a-dihydrothiazolo[4,5-d]pyrimidine-2,7-dione.

Example 15

¹H NMR (400 MHz, CD₃OD) δ ppm: 8.22 (s, 1H), 8.08 (m, 2H), 7.63 (m, 1H), 7.50 (m, 2H), 6.07 (d, J=8.0 Hz, 1H), 5.55 (d, J=4.8 Hz, 1H), 5.33 (dt, J=8.8, 4.4 Hz, 1H), 4.95 (q, J=7.3 Hz, 1H), 3.55 (s, 3H), 2.79 (m, 2H), 1.93 (m, 2H), 1.00 (t, J=7.4 Hz, 3H). MS obsd. (ESI⁺) [(M+H)⁺]: 491.

Example 16

2-[5-(5-Amino-7-hydroxy-2-oxo-thiazolo[4,5-d]pyrimidin-3-yl)-2-(hydroxymethyl)-1,3-oxathiolan-4-yl]-2-methyl-propanoic acid

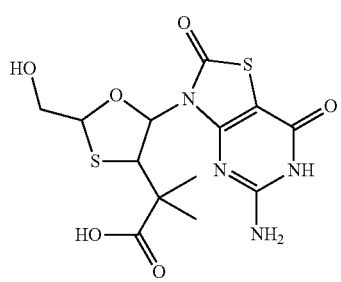 [SMILES: CC(C)(C(=O)O)C1SC(CO)OC1n1c(=O)sc2c(=O)[nH]c(N)nc21]

Preparation of dimethyl 2,2-dimethylbutanedioate (compound 16a)

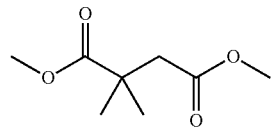

To the solution of 2,2-dimethylsuccinic acid (15.0 g, 0.10 mol) in MeOH (200 mL) was added acetyl chloride (7.1 mL, 0.10 mol) at 0° C. The reaction mixture was stirred at rt overnight. The solvent was removed under reduced pressure to give crude dimethyl 2,2-dimethylbutanedioate (compound 16a) 18.0 g as a colorless oil.

Compound 16a: ¹H NMR (400 MHz, CDCl₃) δ ppm: 3.72 (s, 3H), 3.68 (s, 3H), 2.62 (s, 2H), 1.29 (s, 6H).

Preparation of dimethyl 3-bromo-2,2-dimethyl-butanedioate (compound 16b)

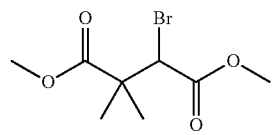

To the solution of diisopropylamine (8.3 mL, 59 mmol) in THF (200 mL) was added n-BuLi (1.6 M in hexane, 37 mL, 59 mmol) at −78° C. under argon. After being stirred at −78° C. for 30 min, dimethyl 2,2-dimethylbutanedioate (compound 16a) (8.0 g, 45 mmol) in THF (50 mL) was added dropwise. After being stirred for another 30 min, TMSCl (10.4 mL, 82 mmol) was added dropwise. The reaction mixture was kept being stirred at −78° C. for 30 min, then NBS (9.7 g, 54 mmol) was added. The reaction mixture was continued to be stirred at −78° C. for another 2 h, and then quenched with saturated NH₄Cl. The reaction mixture was extracted with EtOAc (100 mL) three times. The combined organic layer was washed with saturated NH₄Cl, H₂O and brine, dried over Na₂SO₄, filtered and concentrated to give crude dimethyl 3-bromo-2,2-dimethyl-butanedioate (compound 16b) 11.0 g as a yellowish oil.

Compound 16b: ¹H NMR (400 MHz, CDCl₃) δ ppm: 4.74 (s, 1H), 3.79 (s, 3H), 3.74 (s, 3H), 1.44 (s, 3H), 1.42 (s, 3H).

Preparation of dimethyl 3-acetylsulfanyl-2,2-dimethyl-butanedioate (compound 16c)

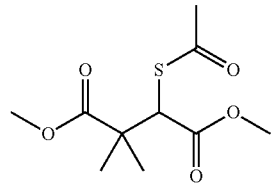

To the solution of dimethyl 3-bromo-2,2-dimethyl-butanedioate (compound 16b) (11.0 g, 62 mmol) in DMF (100 mL) was added potassium thioacetate (8.54 g, 75 mmol). The reaction mixture was stirred at 60° C. for 16 h. After being cooled to rt, the reaction was quenched with saturated NH₄Cl, then diluted with EtOAc (300 mL). The organic layer was washed with saturated NH₄Cl, H₂O and brine, dried with Na₂SO₄, filtered and concentrated to give crude dimethyl 3-acetylsulfanyl-2,2-dimethyl-butanedioate (compound 16c) 11.0 g as a brown oil.

Compound 16c: $^1$H NMR (400 MHz, CDCl$_3$) δ ppm: 4.66 (s, 1H), 3.71 (s, 3H), 3.70 (s, 3H), 2.40 (s, 3H), 1.31 (s, 3H), 1.27 (s, 3H).

Preparation of 2,2-dimethyl-3-sulfanyl-butanedioic acid (compound 16d)

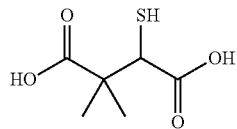

Dimethyl 3-acetylsulfanyl-2,2-dimethyl-butanedioate (compound 16c) (5.0 g, 20 mmol) was dissolved in 6N HCl/dioxane (v/v=1:1, 40 mL). The reaction mixture was heated at 90° C. for 16 h, then the solvent was removed under reduced pressure to give crude 2,2-dimethyl-3-sulfanyl-butanedioic acid (compound 16d) 4.5 g as a brown oil.

Compound 16d: $^1$H NMR (400 MHz, CDCl$_3$) δ ppm: 3.76 (d, J=7.0 Hz, 1H), 1.43 (s, 3H), 1.41 (s, 3H).

Preparation of 2-[2-(benzoyloxymethyl)-5-oxo-1,3-oxathiolan-4-yl]-2-methyl-propanoic acid (16e)

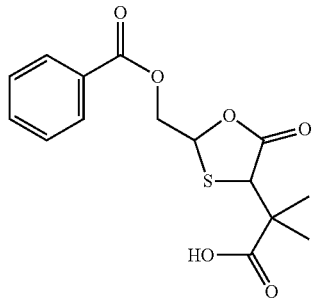 [SMILES: CC(C)(C(=O)O)C1SC(COC(=O)c2ccccc2)OC1=O]

A mixture of benzoyloxy acetaldehyde (3.4 g, 20 mmol) and 2,2-dimethyl-3-sulfanyl-butanedioic acid (compound 16d) (3.6 g, 20 mmol) was stirred at 60° C. in toluene (50 mL) under catalytic amount of p-TsOH (300 mg, 1.7 mmol) for 4 h. After the reaction was completed, the mixture was cooled to rt and diluted with EtOAc (100 mL), washed with saturated NaHCO₃ and brine. The organic layer was dried over Na₂SO₄, filtered and concentrated to give the crude product which was purified by column chromatography to give 2-[2-(benzoyloxymethyl)-5-oxo-1,3-oxathiolan-4-yl]-2-methyl-propanoic acid (compound 16e) 4.0 g as a colorless oil.

Compound 16e: $^1$H NMR (400 MHz, CDCl$_3$) δ ppm: 8.08 (m, 2H), 7.62 (m, 1H), 7.49 (m, 2H), 5.72 (m, 1H), 4.58 (m, 3H), 1.39-1.49 (m, 6H).

Preparation of [4-(2-methoxy-1,1-dimethyl-2-oxo-ethyl)-5-oxo-1,3-oxathiolan-2-yl]methyl benzoate (compound 16f)

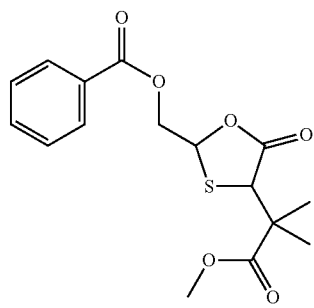 [SMILES: COC(=O)C(C)(C)C1SC(COC(=O)c2ccccc2)OC1=O]

To the solution of 2-[2-(benzoyloxymethyl)-5-oxo-1,3-oxathiolan-4-yl]-2-methyl-propanoic acid (compound 16e) (1.8 g, 5.5 mmol) in DMF (30 mL) was added CDI (1.8 g, 11 mmol) and catalytic amount of DMAP (180 mg, 1.5 mmol). The mixture was stirred at 55° C. for 1.5 h, and then MeOH (0.88 mL, 22 mmol) was added. The mixture was stirred at 55° C. for 3 h. After the reaction was completed, the reaction was quenched with saturated NH₄Cl, and extracted with EtOAc. The combined organic layer was washed with saturated NH₄Cl, H₂O and brine, dried over Na₂SO₄, filtered and concentrated to give the crude product which was purified by column chromatography to afford [4-(2-methoxy-1,1-dimethyl-2-oxo-ethyl)-5-oxo-1,3-oxathiolan-2-yl]methyl benzoate (compound 16f) 1.0 g as a colorless oil.

Compound 16f: $^1$H NMR (400 MHz, CDCl$_3$) δ ppm: 8.07 (m, 2H), 7.61 (m, 1H), 7.49 (m, 2H), 5.71 (t, J=5.3 Hz, 1H), 4.51-4.61 (m, 3H), 3.77 (m, 3H), 1.36-1.45 ppm (m, 6H).

Preparation of [5-acetoxy-4-(2-methoxy-1,1-dimethyl-2-oxo-ethyl)-1,3-oxathiolan-2-yl]methyl benzoate (compound 16g)

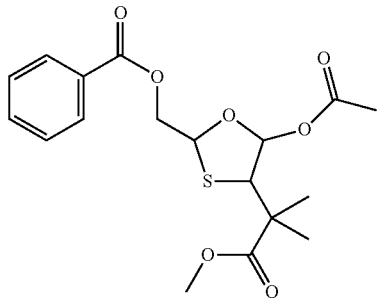 [SMILES: COC(=O)C(C)(C)C1SC(COC(=O)c2ccccc2)OC1OC(C)=O]

To a solution of [4-(2-methoxy-1,1-dimethyl-2-oxo-ethyl)-5-oxo-1,3-oxathiolan-2-yl]methyl benzoate (compound 16f) (600 mg, 1.8 mmol) in anhydrous THF (10 mL) was added LiAlH(Ot-Bu)₃ (1 M in THF, 2.7 mL, 2.7 mmol) dropwise at −78° C. After being stirred at rt for 2 h, pyridine (0.7 mL, 8.7 mmol), acetic anhydride (0.85 mL, 8.7 mmol) and DMAP (0.66 g, 5.1 mmol) were added. The reaction mixture was stirred at rt for 5 h and then quenched with saturated NH₄Cl. The solution was extracted with DCM (30 mL) three times. The organic layer was combined, washed with brine, dried over Na$_2$SO$_4$, filtered and concentrated to give the crude product which was purified by flash column chromatography to afford [5-acetoxy-4-(2-methoxy-1,1-dimethyl-2-oxo-ethyl)-1,3-oxathiolan-2-yl]methyl benzoate (compound 16g) 630 mg as a yellowish oil. MS obsd. (ESI$^+$) [(M+H)$^+$]: 383.

Preparation of [5-(5-amino-2,7-dioxo-6H-thiazolo[4,5-d]pyrimidin-3-yl)-4-(2-methoxy-1,1-dimethyl-2-oxo-ethyl)-1,3-oxathiolan-2-yl]methyl benzoate (compound 16h)

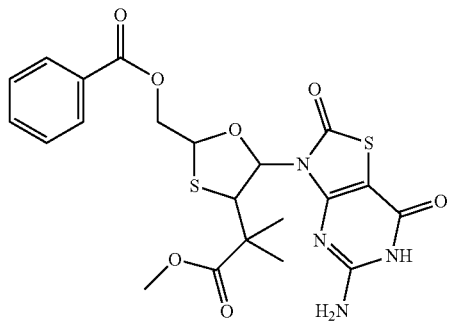 [SMILES: COC(=O)C(C)(C)C1SC(COC(=O)c2ccccc2)OC1n1c(=O)sc2c(=O)[nH]c(N)nc21]

To the suspension of 5-amino-7-hydroxy-3H-thiazolo[4,5-d]pyrimidin-2-one (470 mg, 2.6 mmol) in ACN (20 mL) was added BSA (1.82 g, 2.2 mL, 8.9 mmol). The mixture was stirred under argon at 70° C. for 0.5 h to form a clear solution. The solution was then concentrated under reduced pressure to form a white solid and this solid was dissolved in DCM (20 mL). To the DCM solution was added [5-acetoxy-4-(2-methoxy-2-oxo-ethyl)-1,3-oxathiolan-2-yl] methyl benzoate (compound 16g) (650 mg, 1.7 mmol) and TMSI (680 mg, 472 µL, 3.4 mmol); the reaction mixture was then stirred at rt for 14 h. After the reaction was completed, the mixture was concentrated and the residue was partitioned between EtOAc (50 mL) and saturated NaHCO$_3$ solution (15 mL). The organic layer was separated and the aqueous phase was extracted with EtOAc (25 mL) twice. The combined organic layer was washed with brine, and dried over NaSO$_4$, filtered and concentrated to give crude [5-(5-amino-2,7-dioxo-6H-thiazolo[4,5-d]pyrimidin-3-yl)-4-(2-methoxy-1,1-dimethyl-2-oxo-ethyl)-1,3-oxathiolan-2-yl]methyl benzoate (compound 16h) 860 mg as a brown solid. MS obsd. (ESI$^+$) [(M+H)$^+$]: 507.

Preparation of 2-[5-(5-amino-7-hydroxy-2-oxo-thiazolo[4,5-d]pyrimidin-3-yl)-2-(hydroxymethyl)-1,3-oxathiolan-4-yl]-2-methyl-propanoic acid (Example 16)

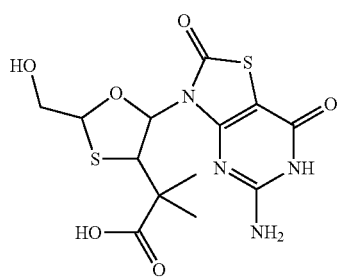 [SMILES: CC(C)(C(=O)O)C1SC(CO)OC1n1c(=O)sc2c(=O)[nH]c(N)nc21]

To the solution of [5-(5-amino-2,7-dioxo-6H-thiazolo[4,5-d]pyrimidin-3-yl)-4-(2-methoxy-1,1-dimethyl-2-oxo-ethyl)-1,3-oxathiolan-2-yl]methyl benzoate (compound 16h) (400 mg, 790 µmol) in THF (10 mL) was added LiOH (227 mg, 9.5 mmol) in water (10 mL). The mixture was then stirred at rt overnight. After the reaction was completed, the mixture was adjusted to pH 7 with HOAc. The mixture was concentrated and purified by preparative HPLC to yield 2-[(cis-2,4-trans-4,5)-5-(5-amino-7-hydroxy-2-oxo-thiazolo[4,5-d]pyrimidin-3-yl)-2-(hydroxymethyl)-1,3-oxathiolan-4-yl]-2-methyl-propanoic acid (Example 16-P1, the diastereomer 1) 12 mg and 2-[(trans-2,4-trans-4,5)-5-(5-amino-7-hydroxy-2-oxo-thiazolo[4,5-d]pyrimidin-3-yl)-2-(hydroxymethyl)-1,3-oxathiolan-4-yl]-2-methyl-propanoic acid (Example 16-P2, the diastereomer 2) 8 mg as white powders. The relative configuration of Example 16-P1 and Example 16-P2 were determined by NOESY.

Example 16-P1

$^1$H NMR (400 MHz, CD$_3$OD) δ ppm: 6.28 (d, J=7.5 Hz, 1H), 5.22 (m, 1H), 5.00 (d, J=7.8 Hz, 1H), 3.83 (m, 1H), 3.74 (m, 1H), 1.31 (m, 6H). MS obsd. (ESI$^+$) [(M+H)$^+$]: 389.

Example 16-P2

$^1$H NMR (400 MHz, CD$_3$OD) δ ppm: 6.42 (d, J=5.5 Hz, 1H), 5.76 (t, J=4.8 Hz, 1H), 4.96 (m, 1H), 3.77 (m, 1H), 3.70 (m, 1H), 1.31 (s, 3H), 1.29 (s, 3H). MS obsd. (ESI$^+$) [(M+H)$^+$]: 389.

Example 16-P1

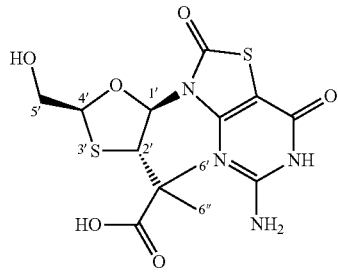

Relative configuration

Example 16-P2

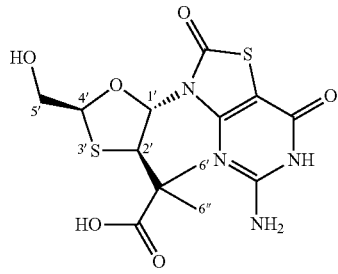

Relative configuration

For Example 16-P1, NOESY correlation of C4'-H and C1'-H was observed, the correlation of C4'-H and C6'-H and C6"-H was observed. For Example 16-P2, the correlation of C4'-H and C2'-H was observed, the correlation of C5'-H and C1'-H was observed.

Example 17

HEK293-Blue-hTLR-7 Cells Assay:

A stable HEK293-Blue-hTLR-7 cell line was purchased from InvivoGen (Cat.#: hkb-htlr7, San Diego, Calif., USA). These cells were designed for studying the stimulation of human TLR7 by monitoring the activation of NF-κB. A SEAP (secreted embryonic alkaline phosphatase) reporter gene was placed under the control of the IFN-3 minimal promoter fused to five NF-κB and AP-1-binding sites. The SEAP was induced by activating NF-κB and AP-1 via stimulating HEK-Blue hTLR7 cells with TLR7 ligands. Therefore the reporter expression was regulated by the NF-κB promoter upon stimulation of human TLR7. The cell culture supernatant SEAP reporter activity was determined using QUANTI-Blue™ kit (Cat.#: rep-qb 1, Invivogen, San Diego, Ca, USA) at a wavelength of 640 nm, a detection medium that turns purple to blue in the presence of alkaline phosphatase.

HEK293-Blue-hTLR7 cells were incubated at a density of 250,000~450,000 cells/mL in a volume of 180 μL in a 96-well plate in Dulbecco's Modified Eagle's medium (DMEM) containing 4.5 g/l glucose, 50 U/ml penicillin, 50 mg/ml streptomycin, 100 mg/ml Normocin, 2 mM L-glutamine, 10% (v/v) heat-inactivated fetal bovine serum for 24 h. Then the HEK293-Blue-hTLR-7 cells were incubated with addition of 20 μL test compound in a serial dilution in the presence of final DMSO at 1% and perform incubation under 37° C. in a $CO_2$ incubator for 20 hours. Then 20 μL of the supernatant from each well was incubated with 180 μL Quanti-blue substrate solution at 37° C. for 1-3 hours and the absorbance was read at 620~655 nm using a spectrophotometer. The signalling pathway that TLR7 activation leads to downstream NF-κB activation has been widely accepted, and therefore similar reporter assay was also widely used for evaluating TLR7 agonist (Tsuneyasu Kaisho and Takashi Tanaka, Trends in Immunology, Volume 29, Issue 7, July 2008, Pages 329.sci; Hiroaki Hemmi et al, Nature Immunology 3, 196-200 (2002).

The compounds of the present invention were tested in the above assay for their TLR7 agonism activity as described herein and results are listed in Table 1. The Examples were found to have $EC_{50}$ of about 3 μM to about 470 M. Particular compounds of formula (I) or (Ia) were found to have $EC_{50}$ of about 3 μM to about 42 M.

TABLE 1

Activity of Compounds in HEK293- hTLR-7 assay

| Example No. | HEK293- hTLR-7 $EC_{50}$ (μM) |
|---|---|
| Example 1-P1 | 317 |
| Example 2-P1 | 144 |
| Example 3-P1 | 469 |
| Example 4-P1 | 13 |
| Example 5-P1 | 24 |
| Example 6-P1 | 23 |
| Example 7-P1 | 28 |
| Example 8-P1 | 2.5 |
| Example 9-P3 | 22 |
| Example 10-P3 | 23 |
| Example 11-P3 | 321 |
| Example 12-P3 | 42 |
| Example 13-P3 | 15 |
| Example 14-P3 | 10 |

Example 18

Metabolism of Prodrugs: Compounds of Formula (II)

A study was undertaken to evaluate the metabolic conversion of prodrugs, compounds of formula (II) or (IIa), to compounds of formula (I) or (Ia) of the present invention. The prodrugs, compounds of formula (II) or (IIa), can be metabolized to the active compound of formula (I) or (Ia) and other compounds of the invention in the body if they are served as prodrugs. Hepatocytes are often used to assess the degree of metabolic conversion of prodrugs in the body of animal or human.

A study was undertaken to evaluate the metabolic conversion of prodrug Example 15, to the corresponding active form, Example 5-P1, in the presence of human hepatocytes. The formation of active form, Example 5-P1, was monitored in the study. For comparison, the metabolic conversion of famciclovir to penciclovir was also assessed.

Hepatocytes Suspension

Cryopreserved hepatocytes plating medium (Cat.#: PY-HMD-03) was purchased from RILD Research Institute for Liver Diseases (Shanghai) Co. Ltd. Cryopreserved human hepatocyte (Cat.#: X008005, Lot#:VRR) was purchased from BioreclamationIVT (Baltimore, Md.).

The stock hepatocyte suspension was prepared from cryopreserved hepatocytes in plating medium at the concentration of $1.8 \times 10^6$ cells/mL.

Working Solutions of Compounds

Compounds were dissolved in DMSO to make 10 mM stock solutions. 10 μL of the stock solution was diluted to 990 μL plating medium to get a 100 μM working solution.

Incubations

Reaction suspensions were prepared in 24-well cell culture plate by mixing 200 μL of hepatocytes suspension (human) and 200 μL of working solution. The final incubation contained $0.9 \times 10^6$ cells/mL and 50 μM compound. The above mixtures were incubated at 37° C. in a humidified 5% $CO_2$ atmosphere, with a 900 rpm shaking.

Preparation of Samples for Analysis

After 180 min of incubation, 200 μL of the incubation mixture was transferred to 1.5 mL tube and quenched with 400 μL stop solution (ice-cold acetonitrile with 0.2 μM Tolbutamide as internal standard). The samples were centrifuged at 14000 rpm for 10 minutes and the resultant supernatants were subjected to LC-MS/MS analysis.

The calibration curves were prepared in the following way. To a 200 μL of cell suspension (cell density of 1.8 million cells/mL), 198 μL of hepatocyte plating medium and 2 μL of the appropriate concentration of the compound in DMSO were added. Samples were mixed thoroughly and 200 μL of the mixture was transferred to 400 μL of the stop solution (see above). The standard curve range is from 1 μM to 25 μM.

Bioanalysis

The compounds were quantified on an API5500 LC-MC/MC instrument in the ESI-Positive MRM mode. The results of prodrug conversion and metabolite generation are summarized in Table 2.

TABLE 2

Concentration of the metabolites formed in human hepatocytes after 3-hour incubation of 50 μM of prodrugs.

| Example No. | Metabolized Product | Product Concentration in human hepatocytes(μM) |
|---|---|---|
| Example 15 | Example 5-P1 | 0.63 |
| Famciclovir | Penciclovir | 18 |

In human hepatocytes, compound Example 15 as well as famciclovir were metabolized to yield the corresponding active metabolites Example 5-P1 and penciclovir, respectively.

The invention claimed is:
1. A compound of formula (I),

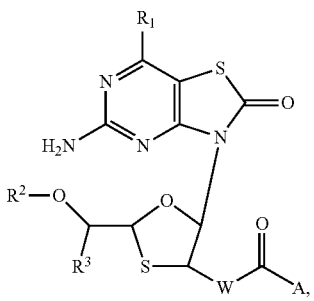

wherein
R$^1$ is OH;
R$^2$ is H;
R$^3$ is H, C$_{1-6}$alkyl, C$_{2-6}$alkenyl or C$_{3-7}$cycloalkyl;
W is —CH$_2$— or —C(C$_{1-6}$alkyl)$_2$—; and
A is OH, C$_{1-6}$alkoxy, C$_{1-6}$alkylNH—, (C$_{1-6}$alkyl)$_2$N— or heterocyclylamino;
or a pharmaceutically acceptable salt, enantiomer or diastereomer thereof.

2. A compound according to claim 1, wherein
R$^1$ is OH;
R$^2$ is H;
R$^3$ is H, methyl, ethyl, butyl, allyl or cyclopropyl;
W is —CH$_2$— or —C(CH$_3$)$_2$—; and
A is OH, methoxy, CH$_3$NH—, (CH$_3$)$_2$N— or morpholinyl;
or a pharmaceutically acceptable salt, enantiomer or diastereomer thereof.

3. A compound according to claim 1 of formula (Ia),

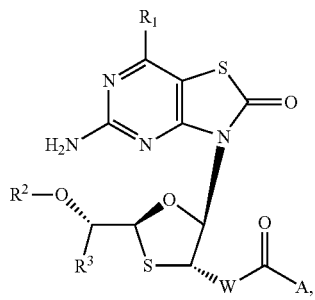

wherein
R$^1$ is OH;
R$^2$ is H;
R$^3$ is H, C$_{1-6}$alkyl, C$_{2-6}$alkenyl or C$_{3-7}$cycloalkyl;
W is —CH$_2$— or —C(C$_{1-6}$alkyl)$_2$-; and
A is OH, C$_{1-6}$alkoxy, C$_{1-6}$alkylNH—, (C$_{1-6}$alkyl)$_2$N— or heterocyclylamino;
or a pharmaceutically acceptable salt, enantiomer or diastereomer thereof.

4. A compound according to claim 3, wherein
R$^1$ is OH;
R$^2$ is H;
R$^3$ is H, methyl, ethyl, butyl, allyl or cyclopropyl;
W is —CH$_2$— or —C(CH$_3$)$_2$—; and
A is OH, methoxy, CH$_3$NH—, (CH$_3$)$_2$N— or morpholinyl;
or a pharmaceutically acceptable salt, enantiomer or diastereomer thereof.

5. A compound according to claim 1, wherein R$^3$ is C$_{1-6}$alkyl, C$_{2-6}$alkenyl or C$_{3-7}$cycloalkyl; or a pharmaceutically acceptable salt, enantiomer or diastereomer thereof.

6. A compound according to claim 1, wherein R$^3$ is methyl, ethyl, cyclopropyl or allyl; or a pharmaceutically acceptable salt, enantiomer or diastereomer thereof.

7. A compound according to claim 1, wherein W is —CH$_2$—; or a pharmaceutically acceptable salt, enantiomer or diastereomer thereof.

8. A compound according to claim 1, wherein
R$^1$ is OH;
R$^2$ is H;
R$^3$ is C$_{1-6}$alkyl or C$_{3-7}$cycloalkyl;
W is —CH$_2$—; and
A is OH, C$_{1-6}$alkoxy, C$_{1-6}$alkylNH—, (C$_{1-6}$alkyl)$_2$N— or morpholinyl;
or a pharmaceutically acceptable salt, enantiomer or diastereomer thereof.

9. A compound according to claim 1, wherein
R$^1$ is OH;
R$^2$ is H;
R$^3$ is methyl, ethyl or cyclopropyl;
W is —CH$_2$—; and
A is OH, methoxy, CH$_3$NH—, (CH$_3$)$_2$N— or morpholinyl;
or a pharmaceutically acceptable salt, enantiomer or diastereomer thereof.

10. A compound according to claim 1 selected from:
Methyl 2-[5-(5-amino-2,7-dioxo-6H-thiazolo[4,5-d]pyrimidin-3-yl)-2-(hydroxymethyl)-1,3-oxathiolan-4-yl]acetate;
Methyl 2-[(trans-2,4-trans-4,5)-5-(5-amino-2,7-dioxo-6H-thiazolo[4,5-d]pyrimidin-3-yl)-2-hydroxymethyl)-1,3-oxathiolan-4-yl]acetate;
2-[5-(5-Amino-2,7-dioxo-6H-thiazolo[4,5-d]pyrimidin-3-yl)-2-(hydroxymethyl)-1,3-oxathiolan-4-yl]acetic acid;
2-[(trans-2,4-trans-4,5)-5-(5-Amino-2,7-dioxo-6H-thiazolo[4,5-d]pyrimidin-3-yl)-2-(hydroxymethyl)-1,3-oxathiolan-4-yl]acetic acid;
2-[5-(5-Amino-2,7-dioxo-6H-thiazolo[4,5-d]pyrimidin-3-yl)-2-(hydroxymethyl)-1,3-oxathiolan-4-yl]-N,N-dimethyl-acetamide;
2-[(trans-2,4-trans-4,5)-5-(5-Amino-2,7-dioxo-6H-thiazolo[4,5-d]pyrimidin-3-yl)-2-(hydroxymethyl)-1,3-oxathiolan-4-yl]-N,N-dimethyl-acetamide;
Methyl 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate;
Methyl 2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate;
2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid;

2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide;
2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide;
5-Amino-3-[(4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione;
5-Amino-3-[(2S,4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione;
Methyl 2-[5-(5-amino-2,7-dioxo-6H-thiazolo[4,5-d]pyrimidin-3-yl)-2-[(1S)-1-hydroxyethyl]-1,3-oxathiolan-4-yl]acetate;
2-[5-(5-Amino-2,7-dioxo-6H-thiazolo[4,5-d]pyrimidin-3-yl)-2-[(1S)-1-hydroxyethyl]-1,3-oxathiolan-4-yl] acetic acid;
2-[5-(5-Amino-2,7-dioxo-6H-thiazolo[4,5-d]pyrimidin-3-yl)-2-[(1S)-1-hydroxypentyl]-1,3-oxathiolan-4-yl] acetic acid;
2-[5-(5-Amino-2,7-dioxo-6H-thiazolo[4,5-d]pyrimidin-3-yl)-2-[(1S)-1-hydroxybut-3-enyl]-1,3-oxathiolan-4-yl]acetic acid;
Methyl 2-[5-(5-amino-2,7-dioxo-6H-thiazolo[4,5-d]pyrimidin-3-yl)-2-[(S)-cyclopropyl(hydroxy)methyl]-1,3-oxathiolan-4-yl]acetate;
2-[5-(5-Amino-2,7-dioxo-6H-thiazolo[4,5-d]pyrimidin-3-yl)-2-[(S)-cyclopropyl(hydroxy)methyl]-1,3-oxathiolan-4-yl]acetic acid; and
2-[5-(5-Amino-7-hydroxy-2-oxo-thiazolo[4,5-d]pyrimidin-3-yl)-2-(hydroxymethyl)-1,3-oxathiolan-4-yl]-2-methyl-propanoic acid;
or a pharmaceutically acceptable salt, enantiomer or diastereomer thereof.

11. A compound according to claim 1 selected from:
2-[5-(5-Amino-2,7-dioxo-6H-thiazolo[4,5-d]pyrimidin-3-yl)-2-(hydroxymethyl)-1,3-oxathiolan-4-yl]acetic acid;
2-[(trans-2,4-trans-4,5)-5-(5-amino-2,7-dioxo-6H-thiazolo[4,5-d]pyrimidin-3-yl)-2-(hydroxymethyl)-1,3-oxathiolan-4-yl]acetic acid;
Methyl 2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate;
Methyl 2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetate;
2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]acetic acid;
2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N-methyl-acetamide;
2-[(4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide;
2-[(2S,4S,5R)-5-(5-amino-2,7-dioxo-6H-thiazolo[4,5-d]pyrimidin-3-yl)-2-[(1S)-1-hydroxypropyl]-1,3-oxathiolan-4-yl]-N,N-dimethyl-acetamide;
5-Amino-3-[(4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione;
5-amino-3-[(2S,4S,5R)-2-[(1S)-1-hydroxypropyl]-4-(2-morpholino-2-oxo-ethyl)-1,3-oxathiolan-5-yl]-6H-thiazolo[4,5-d]pyrimidine-2,7-dione;
2-[5-(5-Amino-2,7-dioxo-6H-thiazolo[4,5-d]pyrimidin-3-yl)-2-[(1S)-1-hydroxyethyl]-1,3-oxathiolan-4-yl] acetic acid; and
2-[5-(5-Amino-2,7-dioxo-6H-thiazolo[4,5-d]pyrimidin-3-yl)-2-[(S)-cyclopropyl(hydroxy)methyl]-1,3-oxathiolan-4-yl]acetic acid;
or a pharmaceutically acceptable salt, enantiomer or diastereomer thereof.

12. A process for the preparation of a compound according to claim 1 comprising the following steps:
(a) the reaction of a compound of formula (XI),

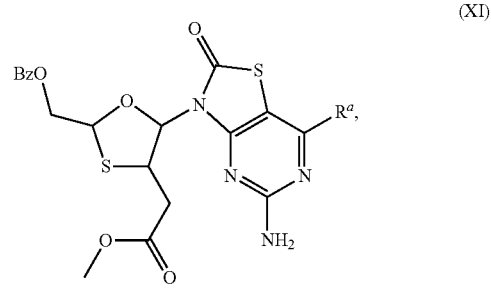

with a base, wherein $R^a$ is $R^1$;
(b) the reaction of a compound of formula (XII),

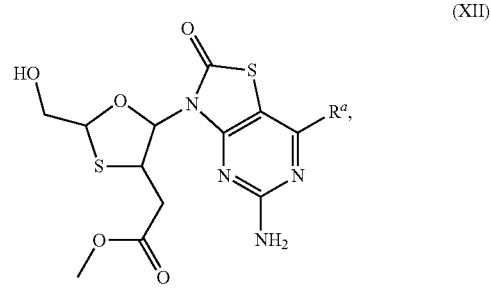

with a base, wherein $R^a$ is $R^1$;
(c) the reaction of a compound of formula (XIII),

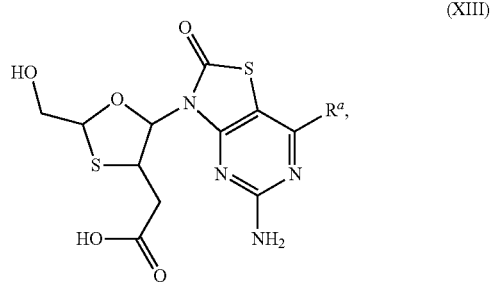

with $R^6R^7NH$ in the presence of coupling reagent, wherein $R^a$ is $R_1$;

(d) the reaction of a compound of formula (P7),

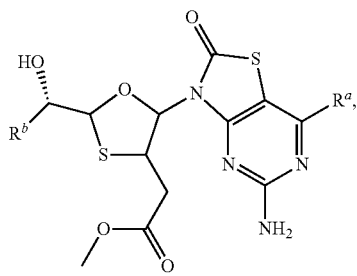
(P7)

with a base, wherein $R^a$ is $R^1$; and $R^b$ is $R^3$;

(e) the reaction of a compound of formula (XXVI),

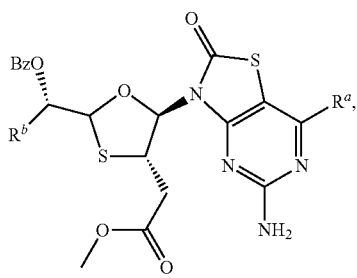
(XXVI)

with a base, wherein $R^a$ is $R^1$; and $R^b$ is $R^3$;

(f) the reaction of a compound of formula (XXVII),

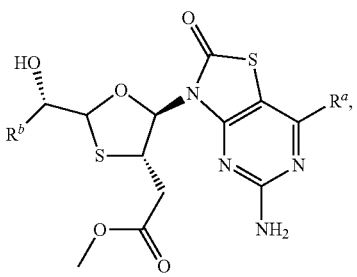
(XXVII)

with a base, wherein $R^a$ is $R^1$; and $R^b$ is $R^3$;

(g) the reaction of a compound of formula (XXVIII),

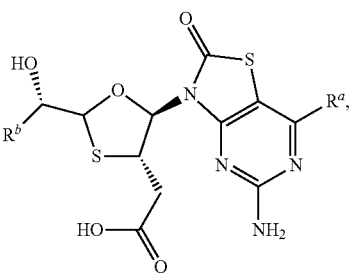
(XXVIII)

with $R^6R^7NH$ in the presence of coupling reagent, wherein $R^a$ is $R^1$; and $R^b$ is $R^3$; or (h) the reaction of a compound of formula (XXV),

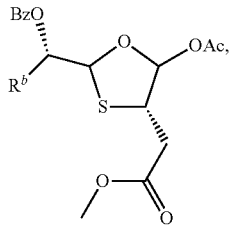
(XXV)

with compound X

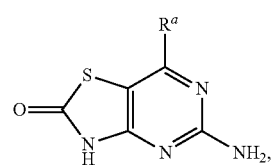
(X)

in the presence of silyl etherification agent and Lewis acid, wherein $R^a$ is $R^1$; and $R^b$ is $R^3$; wherein $R^6$ and $R^7$ are independently selected from H and $C_{1-6}$ alkyl, or together with nitrogen they are attached to form heterocyclylamino.

13. A pharmaceutical composition comprising a compound according to claim 1, or a pharmaceutically acceptable salt, enantiomer or diastereomer thereof, and a therapeutically inert carrier.

14. A compound according to claim 1, or a pharmaceutically acceptable salt, enantiomer or diastereomer thereof, when manufactured according to a process of claim 12.

15. A method for the treatment of hepatitis B virus infection, which method comprises administering a therapeutically effective amount of a compound according to claim 1, or a pharmaceutically acceptable salt, enantiomer or diastereomer thereof.

16. A compound of formula (II),

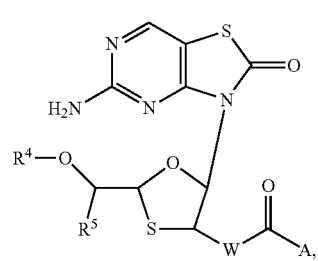
(II)

wherein
$R^4$ is H, $C_{1-6}$alkylcarbonyl, phenylcarbonyl or $C_{1-6}$alkylphenylcarbonyl;
$R^5$ is H, $C_{1-6}$alkyl, $C_{2-6}$alkenyl or $C_{3-7}$cycloalkyl;
W is —$CH_2$— or —$C(C_{1-6}alkyl)_2$-; and
A is OH, $C_{1-6}$alkoxy, $C_{1-6}$alkylNH—, $(C_{1-6}alkyl)_2$N— or heterocyclylamino;
or a pharmaceutically acceptable salt, enantiomer or diastereomer thereof.

17. A compound according to claim 16, wherein
R⁴ is H, acetyl, phenylcarbonyl or methylphenylcarbonyl;
R⁵ is H, methyl, ethyl, butyl, allyl or cyclopropyl;
W is —CH₂— or —C(CH₃)₂—; and
A is OH, methoxy, CH₃NH—, (CH₃)₂N— or morpholinyl;
or a pharmaceutically acceptable salt, enantiomer or diastereomer thereof.

18. A compound of formula (IIa) according to claim 16,

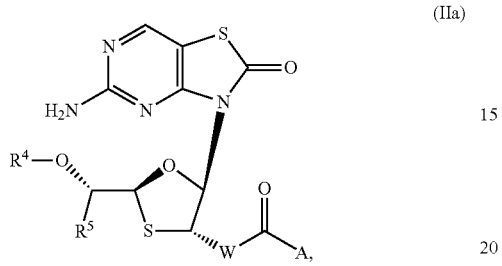

wherein
R⁴ is H, C₁₋₆alkylcarbonyl, phenylcarbonyl or C₁₋₆alkylphenylcarbonyl;
R⁵ is H, C₁₋₆alkyl, C₂₋₆alkenyl or C₃₋₇cycloalkyl;
W is —CH₂— or —C(C₁₋₆alkyl)₂—; and
A is OH, C₁₋₆alkoxy, C₁₋₆alkylNH—, (C₁₋₆alkyl)₂N— or heterocyclylamino;
or a pharmaceutically acceptable salt, enantiomer or diastereomer thereof.

19. A compound according to claim 18, wherein
R⁴ is H, acetyl, phenylcarbonyl or methylphenylcarbonyl;
R⁵ is H, methyl, ethyl, butyl, allyl or cyclopropyl;
W is —CH₂— or —C(CH₃)₂—; and
A is OH, methoxy, CH₃NH—, (CH₃)₂N— or morpholinyl;
or a pharmaceutically acceptable salt, enantiomer or diastereomer thereof.

20. A compound according to claim 16, wherein R⁴ is phenylcarbonyl; or a pharmaceutically acceptable salt, enantiomer or diastereomer thereof.

21. A compound according to claim 16, wherein R⁵ is C₁₋₆alkyl, C₂₋₆alkenyl or C₃₋₇cycloalkyl; or a pharmaceutically acceptable salt, enantiomer or diastereomer thereof.

22. A compound according to claim 16, wherein R⁵ is methyl, ethyl, cyclopropyl or allyl; or a pharmaceutically acceptable salt, enantiomer or diastereomer thereof.

23. A compound according to claim 16, wherein W is —CH₂—; or a pharmaceutically acceptable salt, enantiomer or diastereomer thereof.

24. A compound according to claim 16, wherein
R⁴ is phenylcarbonyl;
R⁵ is C₁₋₆alkyl or C₃₋₇cycloalkyl;
W is —CH₂—; and
A is OH, C₁₋₆alkoxy, C₁₋₆alkylNH—, (C₁₋₆alkyl)₂N— or morpholinyl;
or a pharmaceutically acceptable salt, enantiomer or diastereomer thereof.

25. A compound according to claim 16, wherein
R⁴ is phenylcarbonyl;
R⁵ is methyl, ethyl or cyclopropyl;
W is —CH₂—;
A is OH, methoxy, CH₃NH—, (CH₃)₂N— or morpholinyl;
or a pharmaceutically acceptable salt, enantiomer or diastereomer thereof.

26. A compound according to claim 16 that is [(1S)-1-[(2S,4S,5R)-5-(5-amino-2-oxo-thiazolo[4,5-d]pyrimidin-3-yl)-4-(2-methoxy-2-oxo-ethyl)-1,3-oxathiolan-2-yl]propyl] benzoate; or a pharmaceutically acceptable salt, enantiomer or diastereomer thereof.

27. A process for the preparation of a compound according to claim 16 comprising the following steps:
(a) the reaction of a compound of formula (XI),

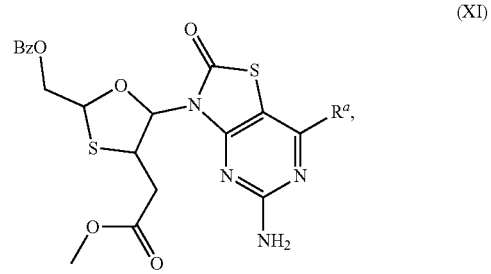

with a base, wherein Rᵃ is H;
(b) the reaction of a compound of formula (XII),

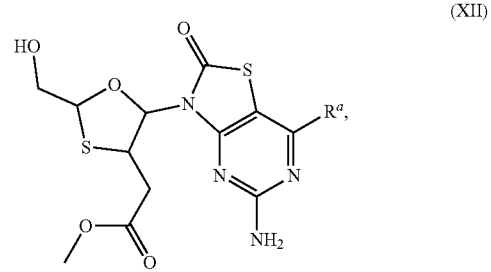

with a base, wherein Rᵃ is H;
(c) the reaction of a compound of formula (XIII),

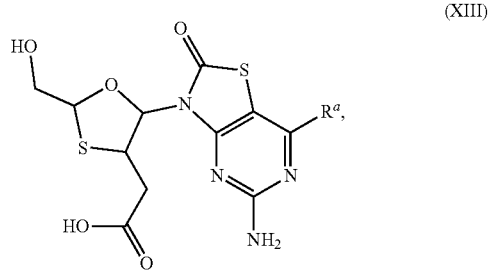

with R⁶R⁷NH in the presence of coupling reagent, wherein Rᵃ is H;
(d) the reaction of a compound of formula (P7),

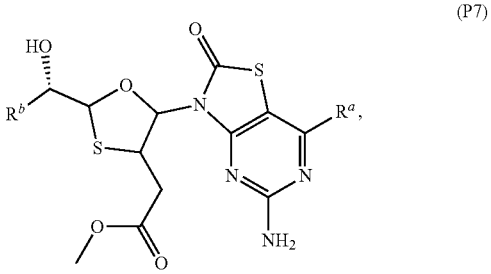

with a base, wherein Rᵃ is H; and Rᵇ is R⁵;

(e) the reaction of a compound of formula (XXVI),

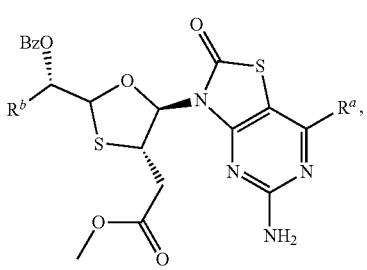

(XXVI)

with a base, wherein $R^a$ is H; and $R^b$ is $R^5$;

(f) the reaction of a compound of formula (XXVII),

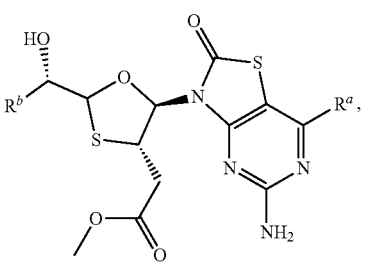

(XXVII)

with a base, wherein $R^a$ is H; and $R^b$ is $R^5$;

(g) the reaction of a compound of formula (XXVIII),

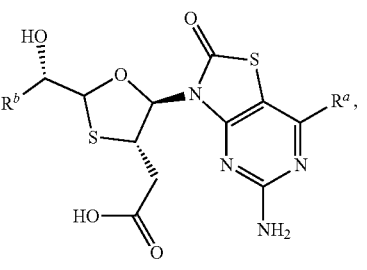

(XXVIII)

with $R^6R^7NH$ in the presence of coupling reagent, wherein $R^a$ is H; and $R^b$ is $R^5$; or (h) the reaction of a compound of formula (XXV),

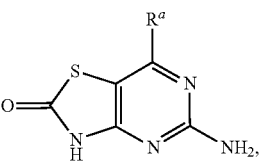

(XXV)

with compound X

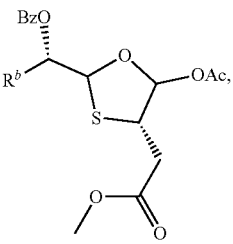

(X)

in the presence of silyl etherification agent and Lewis acid, wherein $R^a$ is H; and $R^b$ is $R^5$;

wherein $R^6$ and $R^7$ are independently selected from H and $C_{1-6}$ alkyl, or together with nitrogen they are attached to form heterocyclylamino.

28. A pharmaceutical composition comprising a compound according to claim 16, or a pharmaceutically acceptable salt, enantiomer or diastereomer thereof, and a therapeutically inert carrier.

29. A compound according to claim 16, or a pharmaceutically acceptable salt, enantiomer or diastereomer thereof, when manufactured according to a process of claim 27.

30. A method for the treatment of hepatitis B virus infection, which method comprises administering a therapeutically effective amount of a compound according to claim 1, or a pharmaceutically acceptable salt, enantiomer or diastereomer thereof.

* * * * *